US011229690B2

(12) United States Patent
Harvill et al.

(10) Patent No.: US 11,229,690 B2
(45) Date of Patent: Jan. 25, 2022

(54) BORDETELLA VACCINE

(71) Applicant: UNIVERSITY OF GEORGIA RESEARCH FOUNDATION, INC., Athens, GA (US)

(72) Inventors: Eric T. Harvill, Watkinsville, GA (US); Monica Cartelle Gestal, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 0 days.

(21) Appl. No.: 16/647,740

(22) PCT Filed: Sep. 28, 2018

(86) PCT No.: PCT/US2018/053413
§ 371 (c)(1),
(2) Date: Mar. 16, 2020

(87) PCT Pub. No.: WO2019/067893
PCT Pub. Date: Apr. 4, 2019

(65) Prior Publication Data
US 2020/0222523 A1    Jul. 16, 2020

Related U.S. Application Data

(60) Provisional application No. 62/564,934, filed on Sep. 28, 2017.

(51) Int. Cl.
| | | |
|---|---|---|
| *A61K 39/10* | (2006.01) | |
| *A61P 31/04* | (2006.01) | |
| *A61K 39/02* | (2006.01) | |
| *A61K 39/00* | (2006.01) | |

(52) U.S. Cl.
CPC ............ *A61K 39/099* (2013.01); *A61P 31/04* (2018.01); *A61K 2039/522* (2013.01); *A61K 2039/543* (2013.01); *A61K 2039/545* (2013.01); *A61K 2039/552* (2013.01)

(58) Field of Classification Search
None
See application file for complete search history.

(56) References Cited

U.S. PATENT DOCUMENTS

2008/0254062 A1    10/2008 Harvill

OTHER PUBLICATIONS

Mattoo et al. Molecular Microbiology. 2004 52:1201-1214.*
Weiss A. (2006) The Genus *Bordetella*. In: Dworkin M., Falkow S., Rosenberg E., Schleifer KH., Stackebrandt E. (eds) The Prokaryotes. Springer, New York, NY. https://doi.org/10.1007/0-387-30745-1_27.*

Abe et al. "The Bordetella Secreted Regulator BspR Is Translocated into the Nucleus of Host Cells via Its N-Terminal Moiety: Evaluation of Bacterial Effector Translocation by the *Escherichia coli* Type III Secretion System." 2015, *PLoS One*. 10(8):e0135140.
Ahuja, et al. "Differential regulation of type III secretion and virulence genes in *Bordetella pertussis* and *Bordetella bronchiseptica* by a secreted anti-σ factor." 2016 *Proc Natl Acad Sci U S A*. 113(9):2341-8.
Bendor et al., "Type Six Secretion System of *Bordetella bronchiseptica* and Adaptive Immune Components Limit Intracellular Survival During Infection," 2015 *PLoS One*; 10:e0140743.
Buboltz et al., "Role of the type III secretion system in a hypervirulent lineage of *Bordetella bronchiseptica*," 2009 *Infect Immun*; 77:3969-3977.
Cotter, et al., "BvgAS-Mediated Signal Transduction: Analysis of Phase-Locked Regulatory Mutants of *Bordetella bronchiseptica* in a Rabbit Model," 1994 *Infection and Immunity*, 62(3):3381-3390.
De Gouw, et al. "Differentially expressed genes in *Bordetella pertussis* strains belonging to a lineage which recently spread globally." 2014 *PLoS One*. 2014;9(1):e84523.
Dewan, et al., "Development of macrolide resistance in *Bordetella bronchiseptica* is associated with the loss of virulence." 2018 *J. Antimicrob Chemother* 73:2797-2805.
Dirix et al., "Both CD4 and CD8 lymphocytes participate in the IFN-gamma response to filamentous hemagglutinin from *Bordetella pertussis* in infants, children, and adults," 2012 *Clin Dev Immunol*. 2012:795958.
Gestal et al., "Immunomodulation as a Novel Strategy for Prevention and Treatment of *Bordetella* spp. Infections." 2019 *Frontiers in Immunology* 10:2869.
Gestal et al., "Enhancement of immune response against *Bordetella* spp. By disrupting immunomodulation." 2019 *Scientific Reports* 9:20261.
Gestal et al., "Integrated Signaling Pathways Mediate *Bordetella* Immunomodulation, Persistence and Transmission" 2019. *Trends Microbiol*. 27(2):118-130.
Hasan et al., "*Bordetella pertussis* adenylate cyclase toxin disrupts functional integrity of bronchial epithelial layers," 2018 *Infect Immun*; 86(3):pii: e00445-17.

(Continued)

*Primary Examiner* — Oluwatosin A Ogunbiyi
(74) *Attorney, Agent, or Firm* — Mueting Raasch Group

(57) ABSTRACT

The present invention provides genetically engineered strains of the *Bordetella* species to include one or more mutations preventing expression of the gene encoding the *Bordetella* Sigma Regulator (also referred to as "bsr," "btrS," and "brpL"), compositions and vaccines thereof, and the use of such engineered strains in methods to protect against *Bordetella* spp, including but not limited to *Bordetella bronchiseptica*, *B. pertussis*, *B. parapertussis*, *B. homelsii*, or *B. avium*. In some aspects, the present invention provides the *Bordetella bronchiseptica* strain RB50Δbsr, compositions and vaccines thereof, and the use of *Bordetella bronchiseptica* strain RB50Δfer in methods to protect against *Bordetella* spp, including but not limited to *Bordetella bronchiseptica*, *B. pertussis*, *B. parapertussis*, *B. homelsii*, or *B. avium*.

18 Claims, 22 Drawing Sheets
Specification includes a Sequence Listing.

(56) References Cited

OTHER PUBLICATIONS

Harvill et al., "Probing the function of *Bordetella bronchiseptica* adenylatecyclase toxin by manipulating host immunity," 1999 *Infect Immun*; 67: 1493-1500.

Hoo, et al., "Evidence for a role of the polysaccharide capsule transport proteins in pertussis pathogenesis." 2014 *PLoS One*. 9(12):e115243.

International Search Report and Written Opinion for PCT/US18/53413 dated Nov. 29, 2018, 9 pages.

International Preliminary Report on Patentability for PCT/US18/53413 dated Mar. 31, 2020, 6 pages.

Kendall "Extra! Extracellular Effector Delivery into Host Cells via the Type 3 Secretion System." 2017 *MBio*. 8(3), e00594-17.

Mann, et al., Use of a Genetically Defined Double Mutant Strain of *Bordetella bronchiseptica* Lacking Adenylate Cyclase and Type III Secretion as a Live Vaccine, Jul. 2007, *Infection and Immunity*, p. 3665-3672.

Mattoo, et al., "Regulation of type III secretion in Bordetella", 2004, *Molecular Biology*, 52(4), 1201-1214,.

Mattoo, et al., Molecular Pathogenesis, Eipdemiology, and Clinical Manifestations of Respiratory Infections Due to *Bordetella pertussis* and other *Bordetella* Subspecies, Apr. 2005, *Clinical Microbiology Reviews*, p. 326-382.

Moon et al., "The BvgAS Regulon of *Bordetella pertussis*", 2017, *Mbio*; 8(5):e01526-17.

Nicholson "Construction and validation of a first-generation *Bordetella bronchiseptica* long-oligonucleotide microarray by transcriptional profiling the Bvg regulon," 2007 *BMC Genomics*. 8:220.

Park et al., "Diversity of secretion systems associated with virulence characteristics of the classical bordetellae." *Microbiology*. 161(12):2328-40.

Sebaihia, et al., "Comparison of the Genome Sequence of the Poultry Pathogen *Bordetella avium* with Those of *B. bronchiseptica, B. pertussis,* and *B. parapertussis* Reveals Extensive Diversity in Surface Structures Associated with Host Interaction", Aug. 2006, *J. of Bacteriology*, 188(16), p. 6002-6015.

Villarino, et al. "The *Bordetella pertussis* type III secretion system tip complex protein Bsp22 is not a protective antigen and fails to elicit serum antibody responses during infection of humans and mice." 2013 *Infect Immun*. 81(8):2761-7.

Weyrich et al., "A Type VI secretion system encoding locus is required for *Bordetella bronchiseptica* immunomodulation and persistence in vivo," 2012 *PloS One*; 7:e45892.

Adkins et al., Bordetella adenylate cyclase toxin differentially modulates toll-like receptor-stimulated activation, migration and T cell stimulatory capacity of dendritic cells. *PLoS One* 9, e104064 (2014).

Alkhalaf et al., Pathogenicity, transmissibility, and tissue distribution of avian pneumovirus in turkey poults. *Avian Dis* 46, 650-659 (2002).

Azuma, Fundamental mechanisms of host immune responses to infection. *J Periodontal Res* 41, 361-373 (2006).

Bannasch et al., Epidemiologic evaluation of multiple respiratory pathogens in cats in animal shelters. *J Feline Med Surg* 7, 109-119 (2005).

Barchtnger et al., sigE facilitates the adaptation of Bordetella bronchiseptica to stress conditions and lethal infection in immunocompromised mice. *BMC Microbiol* 12, 179 (2012),.

Boehm et al., Evaluation of Adenylate Cyclase Toxoid Antigen in Acellular Pertussis Vaccines by Using a Bordetella pertussis Challenge Model in Mice. *Infect Immun* 86, (2018).

Bone et al., Bordetella PlrSR regulatory system controls BvgAS activity and virulence in the lower respiratory tract. *Proc Natl Acad Sci U S A* 114, E1519-E1527 (2017).

Buboltz et al., Replacement of adenylate cyclase toxin in a lineage of Bordetella bronchiseptica. *J Bacteriol* 190, 5502-5511 (2008).

Cattelan et al., Outer membrane protein OmpQ of Bordetella bronchiseptica is required for mature biofilm formation. *Microbiology (Reading)* 162, 351-363 (2016).

Cerny et al., Bordetella pertussis Adenylate Cyclase Toxin Blocks Induction of Bactericidal Nitric Oxide in Macrophages through cAMP-Dependent Activation of the SHP-1 Phosphatase. *J Immunol* 194, 4901-4913 (2015).

Coutts et al., Studies on natural transmission of Bordetella bronchiseptica in cats. *Vet Microbiol* 48, 19-27 (1996).

Cowart et al., Pasteurella multocida and Bordetella bronchiseptica in atrophic rhinitis and pneumonia in swine. *Can J Vet Res* 53, 295-300 (1989).

Cummings et al., Species- and strain-specific control of a complex, flexible regulon by Bordetella BvgAS. *J Bacteriol* 188, 1775-1785 (2006).

Dadaglio et al., Antigen targeting to CD11b+ dendritic cells in association with TLR4/TRIF signaling promotes strong CD8+ T cell responses. *J Immunol* 193, 1787-1798 (2014).

De Jong, Prevention of atrophic rhinitis in piglets by means of intranasal administration of a live non-AR-pathogenic Bordetella bronchiseptica vaccine. *Vet Q* 9, 123-133 (1987).

De Jong et al., A field evaluation of Nobi-Vac atrophic rhinitis vaccine. *Vet Q* 9, 49-59 (1987).

Dewan et al., An Extracellular Polysaccharide Locus Required for Transmission of Bordetella bronchiseptica. *J Infect Dis* 216, 899-906 (2017).

Dunne et al., CD11c+CD8alpha+ dendritic cells promote protective immunity to respiratory infection with Bordetella pertussis. *J Immunol* 183, 400-410 (2009).

El Garch et al., Monitoring of antimicrobial susceptibility of respiratory tract pathogens isolated from diseased cattle and pigs across Europe, 2009-2012: VetPath results. *Vet Microbiol* 194, 11-22 (2016).

Ellis, How well do vaccines for Bordetella bronchiseptica work in dogs? A critical review of the literature 1977-2014, *Vet J* 204, 5-16 (2015).

Elsinghorst, Measurement of invasion by gentamicin resistance. *Methods Enzymol* 236, 405-420 (1994).

Ercoli et al., Intracellular replication of *Streptococcus pneumoniae* inside splenic macrophages serves as a reservoir for septicaemia. *Nat Microbiol* 3, 600-610 (2018).

Fedele et al., Bordetella pertussis commits human dendritic cells to promote a Th1/Th17 response through the activity of adenylate cyclase toxin and MAPK-pathways. *PLoS One* 5, e8734 (2010).

Fennelly et al., Bordetella pertussis expresses a functional type III secretion system that subverts protective innate and adaptive immune responses. *Infect Immun* 76, 1257-1266 (2008).

Feunou et al., T- and B-cell-mediated protection induced by novel, live attenuated pertussis vaccine in mice. Cross protection against parapertussis. *PLoS One* 5, e10178 (2010).

Foley et al., Molecular epidemiology of feline bordetellosis in two animal shelters in California, USA, *Prev Vet Med* 54, 141-156 (2002).

Gaillard et al., Acellular pertussis vaccine based on outer membrane vesicles capable of conferring both long-lasting immunity and protection against different strain genotypes. *Vaccine* 32, 931-937 (2014).

Garbal et al., Occurence of Bordetella bronchiseptica in domestic cats with upper respiratory tract infections. *Pol J Vet Sci* 19, 353-358 (2016).

Gestal et al., Blood or Serum Exposure Induce Global Transcriptional Changes, Altered Antigenic Profile, and Increased Cytotoxicity by Classical Bordetellae. *Front Microbiol* 9, 1969 (2018).

Goebel et al., Bordetella pertussis infection or vaccination substantially protects mice against B, bronchiseptica infection, *PLoS One* 4, e6778 (2009).

Gorgojo et al., Bordetella parapertussis survives inside human macrophages in lipid raft-enriched phagosomes. *Infect Immun* 82, 5175-5184 (2014).

Gorgojo et al., Bordetella parapertussis survives the innate interaction with human neutrophils by impairing bactericidal trafficking inside the cell through a lipid raft-dependent mechanism mediated by the lipopolysaccharide O antigen. *Infect Immun* 80, 4309-4316 (2012).

(56) References Cited

OTHER PUBLICATIONS

Gorgojo et al., Bordetella parapertussis Circumvents Neutrophil Extracellular Bactericidal Mechanisms. *PLoS One* 12, e0169936 (2017).
Halim et al., Isolation and Characterization of Mouse Innate Lymphoid Cells. Current Protocols in Immunology, 3.25:1-13, (2014).
Hanawa et al., Role of Bordetella pertussis RseA in the cell envelope stress response and adenylate cyclase toxin release. *Pathog Dis* 69, 7-20 (2013).
Helps et al., Factors associated with upper respiratory tract disease caused by feline herpesvirus, feline calicivirus, Chlamydophila felis and Bordetella bronchiseptica in cats: experience from 218 European catteries. *Vet Rec* 156, 669-673 (2005).
Hester et al., Host Specificity of Ovine Bordetella parapertussis and the Role of Complement. *PLoS One* 10, e0130964 (2015).
Hester et al., Identification of a CO2 responsive regulon in Bordetella. *PLoS One* 7, e47635 (2012).
Hickey et al., Adenylate cycalse toxin of Bordetella pertussis inhibits TLR-induced IRF-1 and IRF-8 activation and IL-12 production and enhances IL-10 through MAPK activation in dendritic cells. *J Leukoc Biol* 84, 234-243 (2008).
Higgs et al., Immunity to the respiratory pathogen Bordetella pertussis. *Mucosal Immunol* 5, 485-500 (2012).
Hoo et al., "Evidence for a Role of the Polysaccharide Capsule Transport Proteins in Pertussis Pathogenesis" PLOS One, 9(12): e115243 (2014).
Hopkins et al., A survey of infectious diseases in wild turkeys (*Meleagridis gallopavo* silvestris) from Arkansas. *J Wildl Dis* 26, 468-472 (1990).
Horiguchi, Swine atrophic rhinitis caused by pasteurella multocida toxin and bordetella dermonecrotic toxin, *Curr Top Microbiol Immunol* 361, 113-129 (2012).
Houghten et al., Efficacy in turkeys of spray vaccination with a temperature-sensitive mutant of Bordetella avium (Art Vax), *Avian Dis* 31, 309-314 (1987).
Inatsuka et al., Pertactin is required for Bordetella species to resist neutrophil-mediated clearance. *Infect Immun* 78, 2901-2909 (2010).
Jiang et al., In vitro study of the immune stimulating activity of an atrophic [correction of athrophic] rhinitis vaccine associated to chitosan microspheres. *Eur J Pharm Biopharm* 58, 471-476 (2004).
Kang et al., Chitosan microspheres containing Bordetella bronchiseptica antigens as novel vaccine against atrophic rhinitis in pigs. *J Microbiol Biotechnol* 18, 1179-1185 (2008).
Kilgore et al., Pertussis: Microbiology, Disease, Treatment, and Prevention. *Clin Microbiol Rev* 29, 449-486 (2016).
Kirimanjeswara et al., Pertussis toxin inhibits neutrophil recruitment to delay antibody-mediated clearance of Bordetella pertussis. *J Clin Invest* 115, 3594-3601 (2005).
Kirimanjeswara et al., The complex mechanism of antibody-mediated clearance of Bordetella from the lungs requires TLR4. *J Immunol* 175, 7504-7511 (2005).
Lamberti et al., Intracellular trafficking of Bordetella pertussis in human macrophages. *Infect Immun* 78, 907-913 (2010).
Leef et al., Protective immunity to Bordetella pertussis requires both B cells and CD4(+) T cells for key functions other than specific antibody production. *J Exp Med* 191, 1841-1852 (2000).
Leissinger et al., What is your diagnosis? Equine transtracheal wash fluid. *Vet Clin Pathol* 42, 529-530 (2013).
Libster et al., Re-emergence of pertussis: what are the solutions? *Expert Rev Vaccines* 11, 1331-1346 (2012).
Linz et al., Acquisition and loss of virulence-associated factors during genome evolution and speciation in three clades of Bordetella species. bmc Genomics 17, 767 (2016).
Liu et al., New concepts in immunity to Neisseria gonorrhoeae: innate responses and suppression of adaptive immunity favor the pathogen, not the host. *Front Microbiol* 2, 52 (2011).
Liu et al., Neisseria gonorrhoeae selectively suppresses the development of Th1 and Th2 cells, and enhances Th17 cell responses, through TGF-beta-dependent mechanisms. *Mucosal Immunol* 5, 320-331 (2012).
Liu et al., Suppression of host adaptive immune responses by Neisseria gonorrhoeae: role of interleukin 10 and type 1 regulatory T cells. *Mucosal Immunol* 7, 165-176 (2014).
Loving et al., Influenza virus coinfection with Bordetella bronchiseptica enhances bacterial colonization and host responses exacerbating pulmonary lesions. *Microb Pathog* 49, 237-245 (2010).
Maecker et al., Standardization of cytokine flow cytometry assays. *BMC Immunol* 6, 13 (2005).
Mcguirk et al., Pathogen-specific T regulatory 1 cells induced in the respiratory tract by a bacterial molecule that stimulates interleukin 10 production by dendritic cells: a novel strategy for evasion of protective T helper type 1 responses by Bordetella pertussis. *J Exp Med* 195, 221-231 (2002).
Mchale et al., A divergent pseudoglandular configuration of cutaneous plasmacytoma in dogs. *J Vet Diagn Invest* 30, 260-262 (2018).
Mckeithen et al., The emerging role of ASC in dendritic cell metabolism during Chlamydia infection, *PLoS One* 12, e0188643 (2017).
Mohan et al., Bordetella bronchiseptica from aborted equine foetus. *Trop Anim Health Prod* 23, 155-156 (1991).
Nicholson et al., The Bordetella bronchiseptica type III secretion system is required for persistence and disease severity but not transmission in swine. *Infect Immun* 82, 1092-1103 (2014).
Nicholson et al., Microarray and functional analysis of growth phase-dependent gene regulation in Bordetella bronchiseptica. *Infect Immun* 77, 4221-4231 (2009).
Palzer et al., Associations between pathogens in healthy pigs and pigs with pneumonia. *Vet Rec* 162, 267-271 (2008).
Perez Vid Ako Vics et al., Adenylate cyclase influences filamentous haemagglutinin-mediated attachment of Bordetella pertussis to epithelial alveolar cells. *FEMS Immunol Med Microbiol* 48, 140-147 (2006).
Perkins et al., Bordetella pertussis adenylate cyclase toxin (ACT) induces cyclooxygenase-2 (COX-2) in murine macrophages and is facilitated by ACT interaction with CD11b/CD18 (Mac-1) *Mol Microbiol* 66, 1003-1015 (2007).
Pilione et al., The Bordetella bronchiseptica type III secretion system inhibits gamma interferon production that is required for efficient antibody-mediated bacterial clearance. *Infect Immun* 74, 1043-1049 (2006).
Pilione et al., pagP is required for resistance to antibody-mediated complement lysis during Bordetella bronchiseptica respiratory infection. *Infect Immun* 72, 2837-2842 (2004).
Pishko et al., Antibody-mediated bacterial clearance from the lower respiratory tract of mice requires complement component C3. *Eur J Immunol* 34, 184-193 (2004).
Preston et al., Bordetella bronchiseptica PagP is a Bvg-regulated lipid A palmitoyl transferase that is required for persistent colonization of the mouse respiratory tract. *Mol Microbiol* 48, 725-736 (2003).
Pruller et al., Antimicrobial Susceptibility of Bordetella bronchiseptica Isolates from Swine and Companion Animals and Detection of Resistance Genes. *PLoS One* 10, e0135703 (2015).
Rath et al., Persistent Bordetella bronchiseptica pneumonia in an immunocompetent infant and genetic comparison of clinical isolates with kennel cough vaccine strains. *Clin Infect Dis* 46, 905-908 (2008).
Rolin et al., Enzymatic modification of lipid A by ArnT protects Bordetella bronchiseptica against cationic peptides and is required for transmission. *Infect Immun* 82, 491-499 (2014).
Rolin et al., Toll-like receptor 4 limits transmission of Bordetella bronchiseptica. *PLoS One* 9, e85229 (2014).
Ross et al., Adenylate cyclase toxin from Bordetella pertussis synergizes with lipopolysaccharide to promote innate interleukin-10 production and enhances the induction of Th2 and regulatory T cells. *Infect Immun* 72, 1568-1579 (2004).
Siciliano et al., Bordetella bronchiseptica modulates macrophage phenotype leading to the inhibition of CD4+ T cell proliferation and the initiation of a Th17 immune response. *J Immunol* 177, 7131-7138 (2006).

(56) References Cited

OTHER PUBLICATIONS

Skinner et al., Bordetella type III secretion modulates dendritic cell migration resulting in immunosuppression and bacterial persistence. *J Immunol* 175, 4647-4652 (2005).

Skinner et al., Bordetella type III secretion and adenylate cyclase toxin synergize to drive dendritic cells into a semimature state. *J Immunol* 173, 1934-1940 (2004).

Smallridge et al., Different effects of whole-cell and acellular vaccines on Bordetella transmission. *J Infect Dis* 209, 1981-1988 (2014).

Smith et al., Immunogenicity of killed Bordetella bronchiseptica vaccines in the mouse. *Res Vet Sci* 32, 248-252 (1982).

Stockbauer et al., Bordetella type III secretion induces caspase 1-independent necrosis. *Cell Microbiol* 5, 123-132 (2003).

Storisteanu et al., Evasion of Neutrophil Extracellular Traps by Respiratory Pathogens. *Am J Respir Cell Mol Biol* 56, 423-431 (2017).

Taylor-Mulneix et al., Bordetella bronchiseptica exploits the complex life cycle of Dictyostelium discoideum as an amplifying transmission vector. *PLoS Biol* 15, e2000420 (2017).

Thakar et al., Modeling systems-level regulation of host immune responses. *PLoS Comput Biol* 3, e109 (2007).

Tusher et al., Significance analysis of microarrays applied to the ionizing radiation response. *Proc Natl Acad Sci U S A* 98, 5116-5121 (2001).

Vancott et al., Regulation of host immune responses by modification of *Salmonella* virulence genes. *Nat Med* 4, 1247-1252 (1998).

Wakatsuki et al., Cell-surface bound pertussis toxin induces polyclonal T cell responses with high levels of interferon-gamma in the absence of interleukin-12. *Eur J Immunol* 33, 1859-1868 (2003).

Warfel et al., Acellular pertussis vaccines protect against disease but fail to prevent infection and transmission in a nonhuman primate model. *Proc Natl Acad Sci U S A* 111, 787-792 (2014).

Weissenbacher-Lang et al., Retrospective Analysis of Bacterial and Viral Coinfections in Pneumocystis spp. Positive Lung Samples of Austrian Pigs with Pneumonia. *PLoS One* 11, e0158479 (2016).

Weyrich et al., Resident microbiota affect Bordetella pertussis infectious dose and host specificity. *J Infect Dis* 209, 913-921 (2014).

Willems et al., Fimbrial phase variation in Bordetella pertussis: a novel mechanism for transcriptional regulation, *EMBO J* 9, 2803-2809 (1990).

Wolfe et al., IL-10 induction by Bordetella parapertussis limits a protective IFN-gamma response. *J Immunol* 184, 1392-1400 (2010).

Wolfe et al., Clearance of Bordetella parapertussis from the lower respiratory tract requires humoral and cellular immunity. *Infect Immun* 73, 6508-6513 (2005).

Yuk et al., Modulation of host immune responses, induction of apoptosis and inhibition of NF-kappaB activation by the Bordetella type III secretion system. *Mol Microbiol* 35, 991-1004 (2000).

Yuk et al., The BvgAS virulence control system regulates type III secretion in Bordetella bronchiseptica. *Mol Microbiol* 28, 945-959 (1998).

Zhang et al., The O antigen is a critical antigen for the development of a protective immune response to Bordetella parapertussis. *Infect Immun* 77, 5050-5058 (2009).

Zhang et al., O antigen allows B. parapertussis to evade B. pertussis vaccine-induced immunity by blocking binding and functions of cross-reactive antibodies. *PLoS One* 4, e6989 (2009).

Zhao et al., The occurrence of Bordetella bronchiseptica in pigs with clinical respiratory disease. *Vet J* 188, 337-340 (2011).

Zimna et al., Role played by the response regulator Ris in Bordetella bronchiseptica resistance to macrophage killing, *FEMS Microbiol Lett* 201, 177-180 (2001).

Howard et al., "Role of the sRNA bprL in the ability of intracellular survival of Bordetella bronchiseptica" Poster presented at the Science of Veterinary Medicine Symposium on Oct. 13, 2016; University of Georgia, Athens GA, 1 page.

Gestal et al., "Role of sigma factors in colonization and immunity during hostpathogen interaction" Poster presented at the 11th Georgia Glycoscience Symposium on Apr. 25, 2017; University of Georgia, Athens, GA, 1 page.

Gestal et al., "Role of an Uncharacterized Regulatory System in the Development and Progression of Bordetella bronchisep1ca Pathogenesis" Poster presented at the American Society of Microbiology (ASM) Meeting on Jun. 3, 2017. Held Jun. 1-4, 2017 in New Orleans, LA, 1 page.

Howard et al., "Genetic Determinants of Intracellular Survival and Growth of Bordetellae" Poster presented at the Faculty Mentored Undergraduate Research II Infectious Disease Class (IDIS 4970H) on May 12, 2017; University of Georgia, Athens, GA, 11 pages.

* cited by examiner

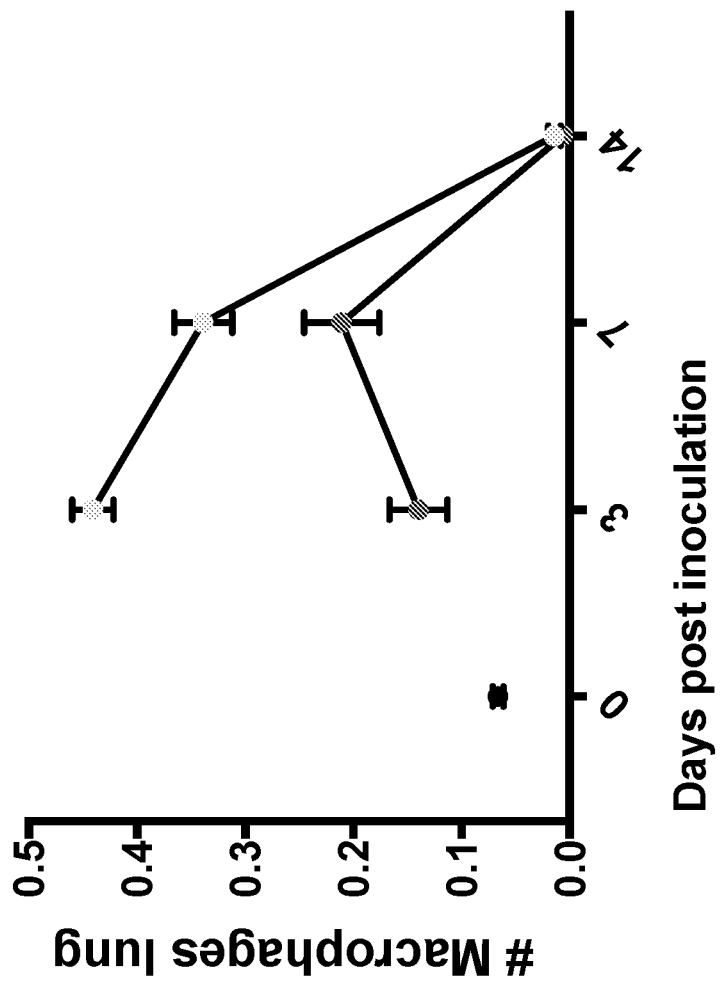

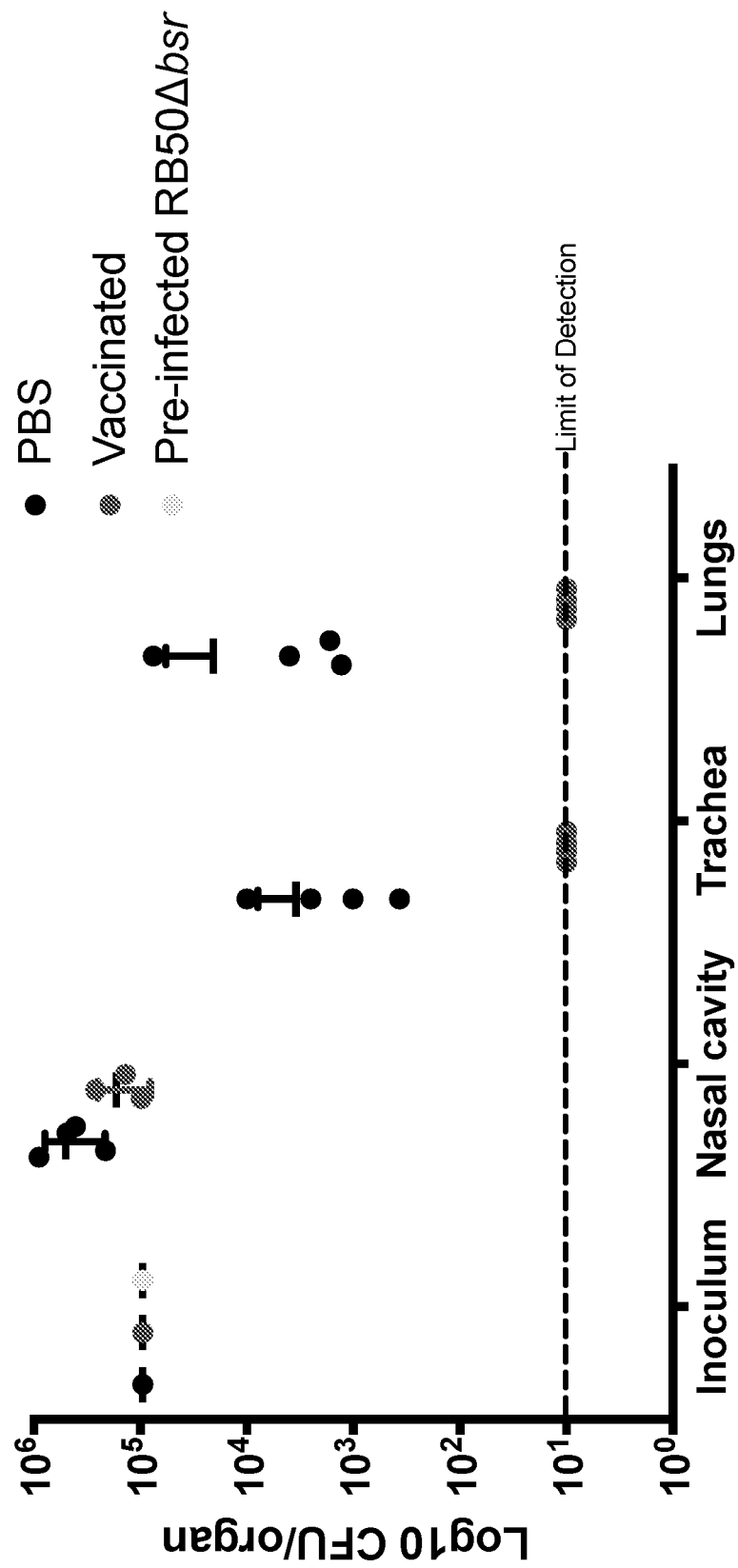

FIG. 3B

*Bordetella pertussis* 7dpi

FIG. 3C

*Bordetella parapertussis* 7dpi

- PBS
- Vaccinated
- Pre-infected RB50Δ*bsr*

Log10 CFU/organ

Inoculum  Nasal cavity  Trachea  Lungs

Limit of detection

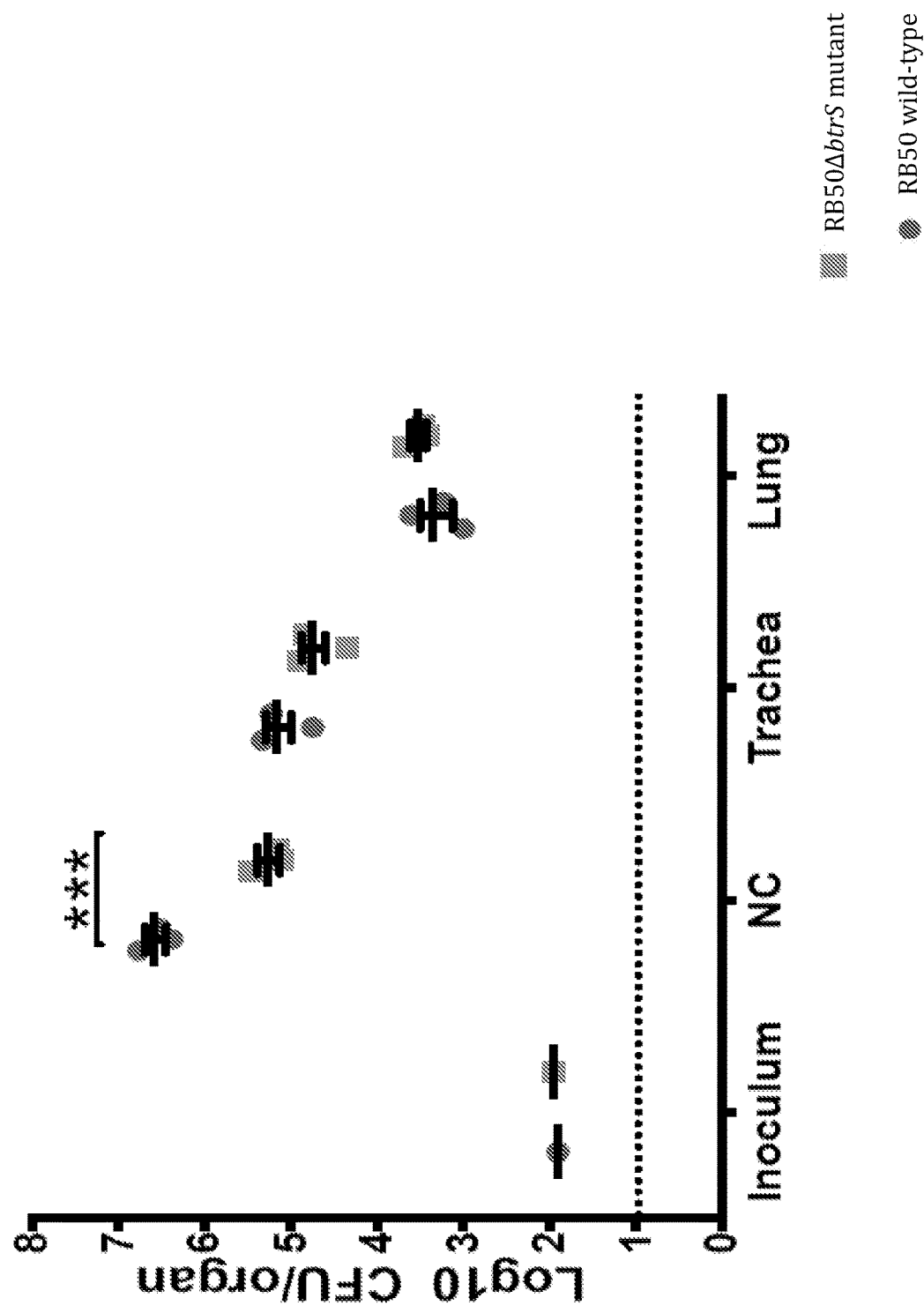

SEQUENCE LISTING

<160> NUMBER OF SEQ ID NOS: 8

<210> SEQ ID NO 1
<211> LENGTH: 24
<212> TYPE: DNA
<213> ORGANISM: artificial
<220> FEATURE:
<223> OTHER INFORMATION: Synthetic primer

<400> SEQUENCE: 1
ggatccgaca gcgtgccgta gggg 24

<210> SEQ ID NO 2
<211> LENGTH: 24
<212> TYPE: DNA
<213> ORGANISM: artificial
<220> FEATURE:
<223> OTHER INFORMATION: Synthetic primer

<400> SEQUENCE: 2
cgtcctccct tggcggcgct gcag 24

<210> SEQ ID NO 3
<211> LENGTH: 22
<212> TYPE: DNA
<213> ORGANISM: artificial
<220> FEATURE:
<223> OTHER INFORMATION: Synthetic primer

<400> SEQUENCE: 3
gaattcgcgg ctgtggcggc cg 22

<210> SEQ ID NO 4
<211> LENGTH: 28
<212> TYPE: DNA
<213> ORGANISM: artificial
<220> FEATURE:
<223> OTHER INFORMATION: Synthetic primer

<400> SEQUENCE: 4
atatgcgttg tccggttttt cgggatcc 28

<210> SEQ ID NO 5
<211> LENGTH: 30
<212> TYPE: DNA
<213> ORGANISM: artificial
<220> FEATURE:
<223> OTHER INFORMATION: Synthetic primer

<400> SEQUENCE: 5
ataggatcca gatcggaacc accagcctgg 30

```
<210> SEQ ID NO 6
<211> LENGTH: 24
<212> TYPE: DNA
<213> ORGANISM: artificial
<220> FEATURE:
<223> OTHER INFORMATION: Synthetic primer

<400> SEQUENCE: 6
attgaattcc ccctgcccgg gcca                                          24

<210> SEQ ID NO 7
<211> LENGTH: 35
<212> TYPE: DNA
<213> ORGANISM: artificial
<220> FEATURE:
<223> OTHER INFORMATION: Synthetic primer

<400> SEQUENCE: 7
atagagctcg caaagcgata ccaagtgaaa gggtg                              35

<210> SEQ ID NO 8
<211> LENGTH: 30
<212> TYPE: DNA
<213> ORGANISM: artificial
<220> FEATURE:
<223> OTHER INFORMATION: Synthetic primer

<400> SEQUENCE: 8
tatactagtc aggcgagcag ttccaggtca                                    30
```

BORDETELLA VACCINE

CONTINUING APPLICATION DATA

This application is the § 371 U.S. National Stage of International Application No. PCT/US2018/053413, filed Sep. 28, 2018, which claims the benefit of U.S. Provisional Application Ser. No. 62/564,934, filed Sep. 28, 2017, which are incorporated by reference herein in their entireties.

GOVERNMENT FUNDING

This invention was made with government support under Grant Nos. CA054660-01, AI122753, and AI116186, all awarded by the National Institutes of Health. The government has certain rights in the invention.

SEQUENCE LISTING

This application contains a Sequence Listing electronically submitted via EFS-Web to the United States Patent and Trademark Office as an ASCII text file entitled "235_02760201_ST25.txt" having a size of 2 kilobytes and created on Sep. 28, 2018. The information contained in the Sequence Listing is incorporated by reference herein.

BACKGROUND

*Bordetella* spp. are gram-negative coccobacilli and are important respiratory pathogens, commonly isolated from the respiratory tract of humans and animals. The genus *Bordetella* is currently subclassified into nine species: *Bordetella pertussis, B. bronchiseptica, B. parapertussis, B. avium, B. hinzii, B. holmesii, B. trematum, B. petrii,* and *B. ansorpii. B. pertussis* and *B. parapertussis* are human pathogens of the respiratory tract and are the etiological agents of whooping cough (pertussis) in humans, although *B. parapertussis* can also cause disease in sheep. *B. bronchiseptica* causes chronic infections in a broad range of animals, including humans. It is also utilized as a model organism for *B. pertussis* as it can more successfully colonize mice, allowing for an efficient model of disease and persistence that mimics pertussis infection in humans.

*B. pertussis* is the major causative agent of whooping cough or pertussis, a highly contagious, acute respiratory disease in humans. There are 50 million cases of whooping cough annually and, according to World Health Organization statistics in 2010, pertussis is one of the ten most common causes of death from infectious disease worldwide, accounting for 300,000-400,000 deaths each year (Libster et al., 2012, *Vaccines;* 11: 1331-1346). The global implementation of pertussis vaccination over the past 60 years has successfully reduced the mortality and incidence rate of pertussis among young children. However, infections with *B. pertussis* still pose an important health burden and cases of pertussis infections in adults have been increasingly reported. This increase of pertussis infections in older age categories represents significant health risks, as they are a source of *B. pertussis* transmission to unvaccinated infants for whom pertussis is a severe, life threatening, disease. The CDC recognizes Whooping cough as a reemerging infectious disease. Despite an extensive vaccination regimen and continued high levels of vaccine coverage, the prevalence of pertussis infection has dramatically increased throughout the industrial world in recent years, leading to epidemics in the U. S. and other countries. The cause of this reemergence is not understood. Although a whole cell vaccine against *Bordetella pertussis* (BP) was introduced over 60 years ago and greatly decreased the number of infections in high-income countries, due to unwanted side effects, it was replaced in the mid-90's by acellular vaccines which contain only 3 to 5 proteins. Since then, despite continued high rates of vaccination, the prevalence of pertussis infection has dramatically increased throughout recent years, leading to dramatic epidemics in several developed countries, including the U.S.

Thus, current pertussis vaccination strategies must be improved and there is a need for the development of new pertussis vaccine candidates.

Bordetellosis also affects a broad range of animals increasing morbidity and mortality, resulting in significant economic burden. In agricultural settings *Bordetella* spp. can infect a variety of animals, including but not limited to pigs, poultry, rabbits, cattle, horse, and sheep. Pigs infected with *B. bronchiseptica* suffer respiratory symptoms including but not limited to atrophic rhinitis, porcine respiratory disease complex, or pneumonia, causing great economic loss due to the increase in morbidity and mortality. Recent studies have shown increasing resistance to antibiotics, including penicillin and cephalosporin, in swine isolates of *B. bronchiseptica*. In many instances, *B. bronchiseptica* infection occurs as co-infection with several pathogens, such as flu and other viruses, *Streptococcus suis, Haemophilus parasuis, Escherichia coli, Pseudomonas multocida, Pneumocystis* spp., or *Mycoplasma hyopneumoniae*. Such co-infection causes an increase in the mortality rates and increases the economic.

Current vaccines against *B. bronchiseptica* confer limited protection, if any, to cats and dogs and there is no approved vaccine available for sheep, horse and other farming animals. Thus, there is a need for new vaccines that can confer protection against *Bordetella*-caused disease in agricultural, equine and poultry settings.

SUMMARY OF THE INVENTION

The present invention includes an isolated strain of the *Bordetella* species, the isolated strain of the *Bordetella* species having a mutation preventing expression of the bsr sigma factor (also referred to as the btrS gene product or the brpL gene product). In some aspects, the mutation is an in frame deletion of the gene encoding the bsr sigma factor. In some aspects, the *Bordetella* species is selected from *Bordetella bronchiseptica, B. pertussis, B. parapertussis, B. homelsii,* or *B. avium*. In some aspects, the *Bordetella* species includes *Bordetella bronchiseptica* strain RB50. In some aspects, the *Bordetella* species includes *Bordetella bronchiseptica* and the mutation includes an in frame deletion of the gene encoding the bsr sigma factor. In some aspects, the *Bordetella* species includes the *Bordetella bronchiseptica* RB50 strain and the mutation includes an in frame deletion of the gene encoding the bsr sigma factor.

The present invention includes a composition including an isolated strain of a *Bordetella* species as described herein. In some aspects, the composition is formulated for intranasal, oral, intradermal, or intramuscular administration.

The present invention includes a vaccine including an isolated strain of a *Bordetella* species as described herein.

The present invention includes a method of generating an immune response to *Bordetella* in a subject, the method including administering an isolated strain of the *Bordetella* species as described herein, or a composition thereof, to the subject. In some aspects, the method includes intranasal, oral, intradermal, or intramuscular administration. In some aspects, the method demonstrates reduced persistence and/or reduced colonization in the lung and/or nasal cavity of the subject. In some aspects, the subject is livestock or domestic pet, including, but not limited to, a cow, pig, chicken, dog, cat, sheep, or horse. In some aspects, the subject is a human.

The present invention includes a method of vaccinating a subject against *Bordetella* infection, the method including administering an isolated strain of the *Bordetella* species as described herein, or a composition thereof, to the subject. In some aspects, the method includes intranasal, oral, intradermal, or intramuscular administration. In some aspects, the method demonstrates reduced persistence and/or reduced colonization in the lung and/or nasal cavity of the subject. In some aspects, the subject is livestock or domestic pet, including, but not limited to, a cow, pig, chicken, dog, cat, sheep, or horse. In some aspects, the subject is a human.

The present invention includes a method of vaccinating a subject against *Bordetella bronchiseptica, B. pertussis, B. parapertussis, B. homelsii*, or *B. avium*, the method including administering an isolated strain of the *Bordetella* species as described herein, or a composition thereof, to the subject. In some aspects, the method includes intranasal, oral, intradermal, or intramuscular administration. In some aspects, the method demonstrates reduced persistence and/or reduced colonization in the lung and/or nasal cavity of the subject. In some aspects, the subject is livestock or domestic pet, including, but not limited to, a cow, pig, chicken, dog, cat, sheep, or horse. In some aspects, the subject is a human.

The present invention includes an isolated *Bordetella bronchiseptica* RB50Δbsr deposited at the ATCC. In some aspects, the present invention includes compositions and vaccines thereof. In some aspects, the present invention includes a method of generating an immune response to *bordetella* in a subject, the method including administering the an isolated *Bordetella bronchiseptica* RB50Δbsr deposited at the ATCC, or a composition thereof, to the subject. In some aspects, the present invention includes a method of vaccinating a subject against a *bordetella* infection, the method including administering the an isolated *Bordetella bronchiseptica* RB50Δbsr deposited at the ATCC, or a composition thereof, to the subject. In some aspects, the present invention includes a method of vaccinating a subject against *Bordetella bronchiseptica, B. pertussis, B. parapertussis, B. homelsii*, or *B. avium*, the method including administering the an isolated *Bordetella bronchiseptica* RB50Δbsr deposited at the ATCC, or a composition thereof, to the subject. In some aspects, the method includes intranasal, oral, intradermal, or intramuscular administration. In some aspects, the method demonstrates reduced persistence and/or reduced colonization in the lung and/or nasal cavity of the subject. In some aspects, the subject is livestock or domestic pet, including, but not limited to, a cow, pig, chicken, dog, cat, sheep, or horse. In some aspects, the subject is a human.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The terms "comprises," and variations thereof, do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIGS. 2A-2C. RB50Δbsr induces higher immune cells recruitment than RB50. C57BL/6J mice were intranasally inoculated with 50 μL of $5 \times 10^7$ bacteria either RB50 or RB50Δbsr. Mice were harvest at days 3, 7, 10, 14, and 21. Spleen and lung were processes following previously published protocols. FIG. 2A shows the number of macrophages isolated from spleen. FIG. 2B shows the number of B cells isolated from spleen. FIG. 2C shows the number of neutrophils isolated from lung (site of infection). The results indicate a higher cell recruitment induced by the bsr mutant suggesting an earlier and stronger response.

FIGS. 3A-3C. RB50Δbsr induces sterilizing immunity against *B. bronchiseptica, B. pertussis*, and *B. parapertussis*. C57BL/6J mice were intranasally inoculated with 50 μL of $5 \times 10^7$ of RB50Δbsr or IP vaccinated with Adacel (2 dosages 14 days apart and diluted 1:5) and a third group was inoculated IP with PBS as a control. 62 days post-inoculation each group of mice were challenged with 50 μL $10^5$ of *B. bronchiseptica, B. pertussis*, or *B. parapertussis*. 7 days post-inoculation mice were euthanized and organs harvested. A control group was challenged first with RB50Δbsr and not re-challenge to confirm clearance. FIG. 3A shows the results obtained for the challenge with *B. bronchiseptica*. FIG. 3B shows the results for the challenge with *B. pertussis*. FIG. 3C shows the result for the challenge with *B. parapertussis*. The results showed that none of the three classical *Bordetellae* colonizes any organ of the mice previously challenged with RB50Δbsr suggesting that previous infection with the bsr mutant provides sterilizing immunity against further encounter with classical *Bordetella* spp.

FIG. 4A shows the log 10 CFU recovered in trachea and lung of mice challenged with RB50. FIG. 4B shows the log 10 CFU of mice challenged with BP536. The results revealed a 3 logs reduction in the CFU of those animals that were passive transferred with antibodies of RB50 Δbsr, indicating that bsr induces a more robust and protective set of antibodies.

FIG. 5. Clearance requires adaptive immunity. Mice were intranasally challenged with 5 μl of PBS containing 150 CFU. In blue is presented RB50 wild-type strain of *B. bronchiseptica* and in red the strain RB50ΔbtrS mutant. In black boxes are indicated the significant differences between both sets of treatments. Statistical difference was determine using Two-Way Anova test ***=p<0.001.

FIG. 6A shows CD4+ numbers (10$^3$) recruited in lungs of mice expose to different bacteria. FIG. 6B shows CD8+ numbers (10$^3$) recruited in lungs of mice expose to RB50, the mutant RB50ΔbtrS or naive group.

FIG. 7A shows B cell numbers in lungs (10$^6$). FIG. 7B shows IgG antibody titers in lungs of infected mice with each strain. FIG. 7C shows IgA antibody titers in lungs of infected mice with each strain.

FIG. 9A shows the workflow of experiment. The top line shows the PBS control group timeline, the middle line shows the Adacel vaccination (⅕ dose) timeline, and the bottom line shows the btrS mutant timeline. Challenge indicates when the mice were expose to a high dose high volume of bacteria. FIG. 9B shows the CFUs of the nasal cavity after challenge with high dose of RB50. Statistical significance was calculated using Two-Way Anova ****=p<0.0001.

FIG. 11A shows the log$_{10}$ CFU values isolated after infection with RB50 *B. bronchiseptica*. FIG. 11B shows the log$_{10}$ CFU values isolated after infection with 536 *B. pertussis*. FIG. 11C shows the log$_{10}$ CFU values isolated after infection with 12822 *B. parapertussis*.

FIG. 12A shows location of the brpL gene in *B. bronchiseptica*. FIG. 12B shows location of the brpL gene in *B. pertussis*. FIG. 12C shows location of shows location of the brpL gene *B. pertussis*.

DETAILED DESCRIPTION OF ILLUSTRATIVE EMBODIMENTS

Figure 1A:
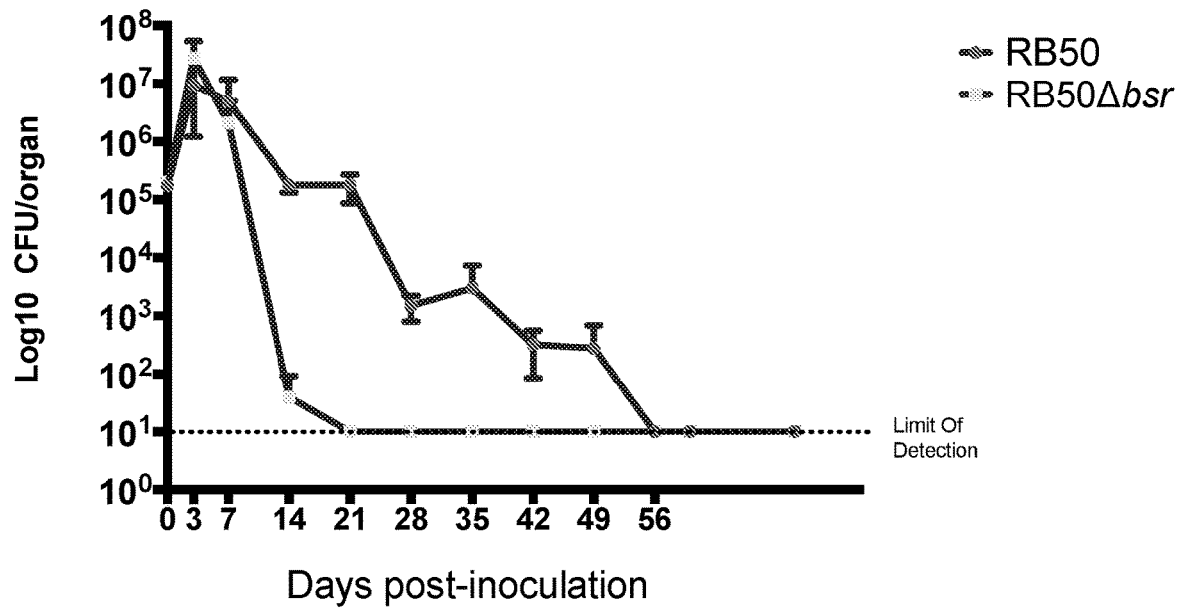
FIGS. 1A-1C. bsr is required to persist in lung and nasal cavity of C57Bl/6J mice. C57BL/6J mice were intranasally inoculated with 50 μL of $5 \times 10^7$ bacteria either RB50 or RB50Δbsr. Mice were harvest at days 3, 7, 10, 14, 21, 28, 35, 42, 49, and 56 and organs were plated in BGS. The results showed that bsr is required to persist in lungs (FIG. 1A), trachea (FIG. 1B) and nasal cavity (FIG. 1C).

The present invention provides genetically engineered strains of the *Bordetella* species, including a mutation preventing expression of the gene encoding the *Bordetella* Sigma Regulator, also referred to herein as "bsr" and the use of such mutant *Bordetella* species as vaccines to protect against *Bordetella* spp. infections. In some aspects, the mutation is an in frame deletion of the gene encoding the bsr sigma factor. The bsr gene encoding the *Bordetella* sigma regulator is also referred to as the btrS gene or the brpL gene.

*Bordetella* spp. are gram-negative coccobacilli and are important respiratory pathogens, commonly isolated from the respiratory tract of humans and animals. The genus *Bordetella* is currently subclassified into nine species: *Bordetella pertussis, B. bronchiseptica, B. parapertussis, B. avium, B. hinzii, B. holmesii, B. trematum, B. petrii, and B. ansorpii*. A *Bordetella* bsr deletion mutant of the present invention includes a bsr deletion of bsr in *B. pertussis, B. bronchiseptica, B. parapertussis, B. avium, B. hinzii, B. holmesii, B. trematum, B. petrii,* or *B. ansorpii*.

A *Bordetella* bsr deletion mutant of the present invention may be, for example, a genetically engineered mutant of *Bordetella bronchiseptica, B. pertussis, B. parapertussis, B. homelsii,* or *B. avium*.

In some aspects, a *Bordetella* bsr deletion mutant may be constructed in the *Bordetella bronchiseptica* strain RB50. *B. bronchiseptica* strain RB50 has been extensively characterized in a variety of animal species. First described by Cotter and Miller, RB50 is a *B. bronchiseptica* strain isolated from the naris of a 3-month-old New Zealand White rabbit. In the Bvg$^+$ phase, RB50 expresses FHA and has hemolytic activity (due to adenylate cyclase toxin) and produces small domed colonies on BG agar. In the Bvg$^-$ phase, resulting from modulation with MgSO$_4$, nicotinic acid, or growth at low temperature, FHA and hemolytic activity are no longer produced, colonies are large and flat, and the phenotype of motility appears. Bvg$^-$-phase RB50 expresses a 40-kDa flagellin protein, which corresponds to one of the two identified *B. bronchiseptica* flagellin isotypes that differ in electrophoretic mobility. Additionally, RB50 is oxidase, catalase, urease, and citrate positive and does not ferment glucose or lactose, characteristics consistent with the identification of this strain as *B. bronchiseptica* (Cotter and Miller, 1994, *Infection and Immunity*, 62(3):3381-3390).

A knock out mutant (in frame deletion) of the brpL gene (also referred to herein as the bsr gene or the btrS gene) may be constructed using standard allelic exchange technology, as previously reported in the literature. See Inatsuka et al., 2010, *Infect Immun;* 78:2901-2909 (doi:10.1128/IAI.00188-10). Primers as detailed in Table 1 of Example 1 may be used. Alternatively, in some applications, UpStream region primers UF_btrS (ATA GGA TCC AGA TCG GAA CCA GCC TGG (SEQ ID NO: 5)) and UR_btrS (ATT GAA TTC CCC CTG CCC GGG CCA (SEQ ID NO: 6)) and DownStream region primers DF_btrS (ATA GAG CTC GCA AAG CGA TAC CAA GTG AAA GGG TG (SEQ ID NO: 7)) and DR_btrS (TAT ACT AGT CAG GCG AGC AGT TCC AGG TCA (SEQ ID NO: 8)) may be used.

Figure 12A:
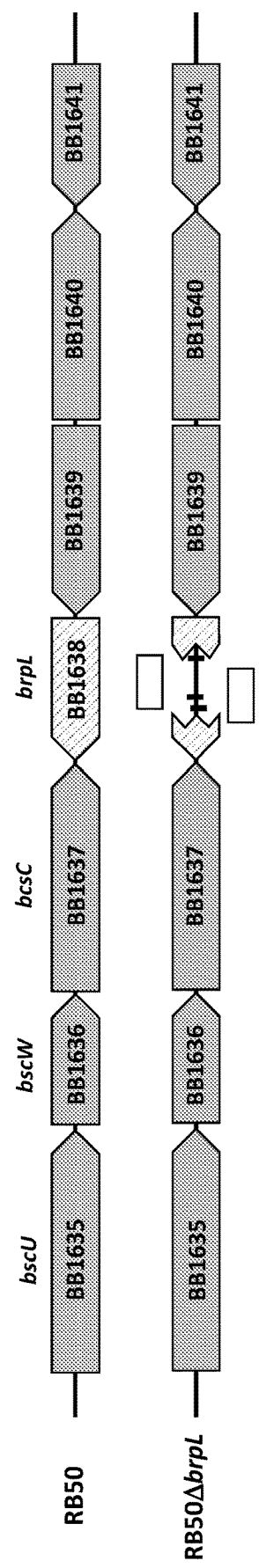
FIG. 12A-12C. Chromosomal location and in-frame deletion mutant of brpL gene.
Figure 12B:
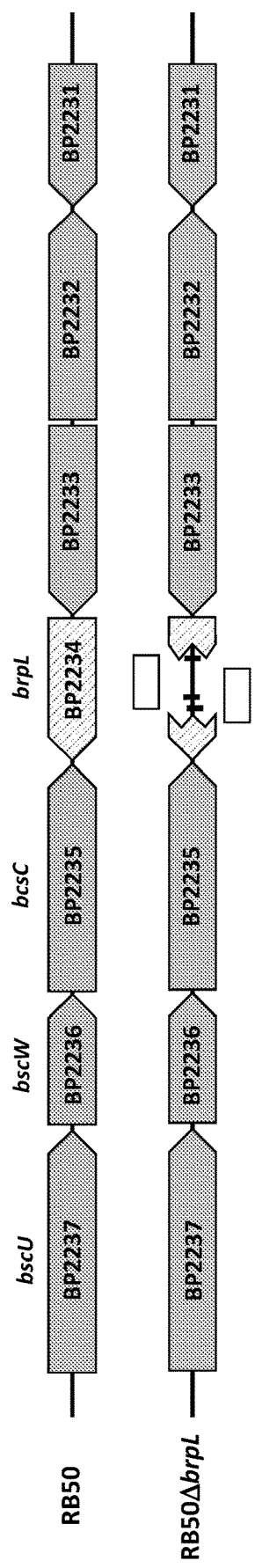
Figure 12C:
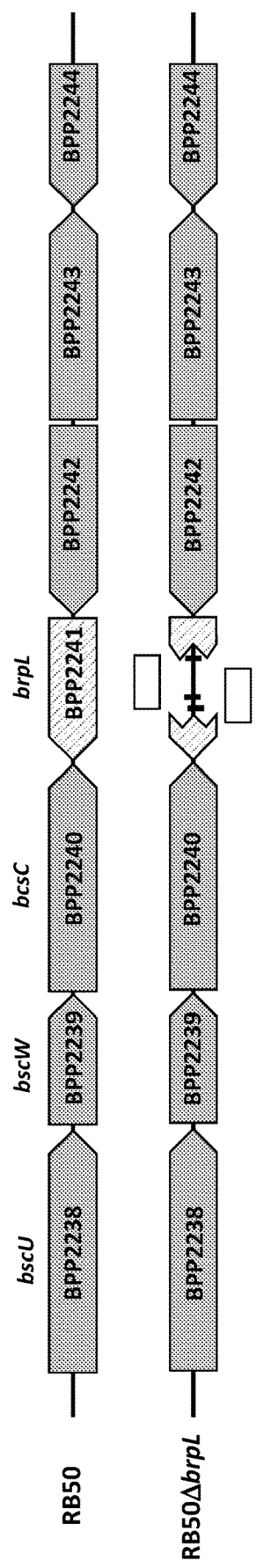

Amongst the regulatory systems are the bacterial sigma factors that can control gene expression by directly binding to the promotor regions of genes. Their activity responds to environmental or developmental signals, changing patterns of gene expression. In *Bordetella* spp., several sigma factors have been reported, one of which is the sigma factor known as brpL. See Moon et al., 2017, *Mbio;* 8(5):e01526-17; Nicholson, 2007, *BMC Genomics;* 8:220; Ahuja et al., 2016, *Proc Natl Acad Sci USA;* 113:2341-2348; and Mattoo et al., 2004, *Mol Microbiol;* 52:1201-1214. This sigma factor plays an important role in the regulation of Type III Secretion System (T3 SS), but it remains unclear what other genes might be regulated by it as well as its particular role during infection it is unknown. The brpL gene (locus_tag BB1638) encodes a BvgAS-regulated extracytoplasmic function (ECF) sigma factor. The brpL gene is located immediately downstream of T3SS (BB1608 to BB1637) in reverse orientation. It is also known as btrS and is the first gene of the btr locus (9 genes) that is involved in transcriptional regulation of the T3SS and other virulence-associated genes (Ahuja et al., 2016, *Proc Natl Acad Sci USA;* 113:2341-2348). Chromosomal locations of the brpL gene are shown in FIGS. 12A-12C.

A *Bordetella* spp. bsr deletion mutant as described herein may be put on deposit with the American Type Culture Collection (ATCC®), 10801 University Boulevard, Manassas, Va. 20110-2209, USA. Such a deposit may be in accordance with the Budapest Treaty on the International Recognition of the Deposit of Microorganisms for the Purposes of Patent Procedure.

In some aspects, the present invention includes the *Bordetella bronchiseptica* strain RB50Δbsr isolate described herein. The *Bordetella bronchiseptica* strain RB50Δbsr isolate described herein may be put on deposit with the American Type Culture Collection (ATCC®), 10801 University Boulevard, Manassas, Va. 20110-2209, USA. Such a deposit may be in accordance with the Budapest Treaty on the International Recognition of the Deposit of Microorganisms for the Purposes of Patent Procedure.

Also included in the present invention are compositions including one or more of the isolated *Bordetella* spp. bsr deletion mutants, as described herein. Such a composition may include a pharmaceutically acceptable carrier. As used, a pharmaceutically acceptable carrier refers to one or more compatible solid or liquid fillers, diluents or encapsulating substances, which are suitable for administration to a human or other vertebrate animal. Carriers include, for example, stabilizers, preservatives and buffers. Suitable stabilizers include, for example, SPGA, carbohydrates (such as sorbitol, mannitol, starch, sucrose, dextran, glutamate or glucose), proteins (such as dried milk serum, albumin or casein) or degradation products thereof. Suitable buffers include, for example, alkali metal phosphates. Suitable preservatives include, for example, thimerosal, merthiolate and gentamicin. Diluents include, but are not limited to, water, aqueous buffer (such as buffered saline), alcohols, and polyols (such as glycerol). Such compositions and/or carriers may be pyrogen free. The formulation of such compositions is well known in the art.

Compositions of the invention may include an adjuvant, including, but not limited to aluminum hydroxide; aluminum phosphate; QS-21 Stimulon; 3-O-deacylated monophosphoryl lipid A; IL-12; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dip-almitoyl-sn-glycero-3-hydroxyphosphoryloxy)-ethylamine (CGP 19835A, referred to a MTP-PE); cholera toxin; and non-toxic derivatives of cholera toxin, including its B subunit; procholeragenoid, and fungal polysaccharides. Compositions of the present invention may include additional active immunogens, including other immunologically active antigens against other pathogenic species. The other immunologically active antigens may be replicating agents or non-replicating agents. The formulation of such compositions is well known in the art.

The present invention also includes methods of making and using the compositions described herein. The compositions of the present disclosure may be formulated in pharmaceutical preparations in a variety of forms adapted to the chosen route of administration. One of skill will understand that the composition will vary depending on mode of administration and dosage unit. The agents of this invention can be formulated for administration in a variety of ways, including, but not limited to, intravenous, topical, oral, intranasal, subcutaneous, intraperitoneal, and intramuscular delivery. In some aspects, a composition is formulated for needle-less administration to the mucosa, for example for intranasal administration to the upper respiratory tract. It is expected that mucosal administration of the pharmaceutical composition to a mammalian subject will stimulate an immune response in mucosal tissues, including mucosal tissues that are remote from the site of administration, in addition to producing a systemic immune response in the subject.

The present invention also includes methods of inducing an immune response in a subject by administering a *Bordetella* spp. bsr deletion mutant or composition, as described herein to the subject. The immune response may or may not confer protective immunity. An immune response may include, for example, a humoral response and/or a cell mediated response. Such an immune response may be a humoral immune response, a cellular immune response, and/or a mucosal immune response. A humoral immune response may include an IgG, IgM, IgA, IgD, and/or IgE response. The determination of a humoral, cellular, or mucosal immune response may be determined by any of a variety of methods, including, but not limited to, any of those described herein. The induction of an immune response may include the priming and/or the stimulation of the immune system to a future challenge with an infectious agent, providing immunity to future infections. The induction of such an immune response may serve as a protective response, generally resulting in a reduction of the symptoms. The immune response may enhance an innate and/or adaptive immune response. Immunogenicity may be assayed in any of a variety of animal models, including, but not limited to, mouse and/or non-human primates model systems, such as the baboon model system.

The present invention also includes methods of vaccinating a subject by administering a *Bordetella* spp. bsr deletion mutant as described herein to the subject. With administration, one or more of the effects described in the Examples included herewith may be observed in the subject.

With the methods of the present invention, any of a variety of modes of administration may be used. For example, administration may be intravenous, topical, oral, intranasal, subcutaneous, intraperitoneal, intramuscular, or intratumor. In some aspects, administration is the needleless administration to a mucosal membrane, for example, by the intranasal administration to the upper respiratory tract by spray, droplet or aerosol or oral, sublingual or buccal administration.

An agent of the present disclosure may be administered at once or may be divided into a number of multiple doses to be administered at intervals of time. For example, agents of the invention may be administered repeatedly, e.g., at least 2, 3, 4, 5, 6, 7, 8, or more times, or may be administered by continuous infusion. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that any concentration ranges set forth herein are exemplary only and are not intended to limit the scope or practice of the claimed compositions and methods.

By a "therapeutically effective amount" is meant a sufficient amount of the compound to treat the subject at a reasonable benefit/risk ratio applicable to obtain a desired therapeutic response. It will be understood, however, that the total daily usage of the compounds and compositions of the present invention will be decided by the attending physician within the scope of sound medical judgment. The specific therapeutically effective dose level for any particular patient will depend upon a variety of factors including, for example, the disorder being treated and the severity of the disorder, activity of the specific compound employed, the specific composition employed, the age, body weight, general health, sex and diet of the patient, the time of administration, route of administration, and rate of excretion of the specific compound employed, the duration of the treatment, drugs used in combination or coincidentally with the specific compound employed, and like factors well known in the medical arts.

In some therapeutic embodiments, an "effective amount" of an agent is an amount that results in a reduction of at least one pathological parameter. Thus, for example, in some aspects of the present disclosure, an effective amount is an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the expected reduction in the parameter in an individual not treated with the agent.

As used herein, the term "subject" includes, but is not limited to, humans and non-human vertebrates. In preferred embodiments, a subject is a mammal, particularly a human. A subject may be an individual. A subject may be an "individual," "patient," or "host." Non-human vertebrates include livestock animals, companion animals, and laboratory animals. Non-human subjects also include non-human primates as well as rodents, such as, but not limited to, a rat or a mouse. Non-human subjects also include, without limitation, chickens, horses, cows, pigs, goats, dogs, cats, guinea pigs, hamsters, ferrets, mink, and rabbits.

As used herein "in vitro" is in cell culture and "in vivo" is within the body of a subject.

As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state. For instance, a polypeptide, a polynucleotide, or a cell can be isolated. Preferably, a substance is purified, i.e., is at least 60% free, preferably at least 75% free, and most preferably at least 90% free from other components with which they are naturally associated.

The present invention is illustrated by the following examples. It is to be understood that the particular examples, materials, amounts, and procedures are to be interpreted broadly in accordance with the scope and spirit of the invention as set forth herein.

EXAMPLES

Example 1

Construction of a RB50ΔbrpL Knock Out in Frame Deletion

A knock out mutant (in frame deletion) of the brpL gene (also referred to herein as the bsr gene or the btrS gene) was constructed and the construction confirmed by PCR followed by whole genome sequencing. The knock out generation utilized standard allelic exchange technology, as previously reported in the literature. See Inatsuka et al., 2010, *Infect Immun;* 78:2901-2909 (doi:10.1128/IAI.00188-10). Briefly, ~500-bp DNA fragments flanking the brpL gene to be deleted were amplified and cloned into the vector, flanking gentamicin resistance gene on both sides. For conjugation, *B. bronchiseptica* was mated with *E. coli* SM10λpir donor strain on BG agar with 50 mM $MgSO_4$, to inhibit expression of the vector-based SceI restriction enzyme. Mutant colonies were subsequently selected for by growth on gentamicin containing BG agar, and incorporation of the mutant allele was verified by PCR. Mutations were complemented using pBBR1 as the vector. The primers used in the generation of this mutant are shown in Table 1.

TABLE 1

| Name | Sequence (5'-3') | Temp. (Celsius) | Fragment size |
|---|---|---|---|
| UP-Fw | GGATCCGACAGCGTGCCGTAGGGG (SEQ ID NO: 1) | 62 | 428 |
| UP-Rv | CGTCCTCCCTTGGCGGCGCTGCAG (SEQ ID NO: 2) | 66 | |

TABLE 1-continued

| Name | Sequence (5'-3') | Temp. (Celsius) | Fragment size |
|---|---|---|---|
| DW-Fw | GAATTCGCGGCTGTGGCGGCCG (SERQ ID NO: 3) | 64 | 550 |
| DW-Rv | ATATGCGTTGTCCGGTTTTTCGGGATCC (SEQ ID NO: 4) | 64 | |

After the allelic exchange, hemolytic colonies were screened by PCR using the same primers expecting changes in band size of the indicated fragment size. Once a clone was selected, it was named RB50ΔbrpL (also referred to herein as RB50Δbsr, RB50ΔbtrS, and BBvac). Frozen stocks were made and sent for confirmation by whole genome sequencing.

The chromosomal location and in-frame deletion mutant of brpL gene is shown in FIGS. 12A-12C and FIG. 13.

Example 2

Genetic Determinants of Intracellular Survival and Growth of *Bordetellae*

This example shows that *Bordetella* species utilize intracellular survival within host immune cells as the mechanism for persisting at undetected levels. This mechanism could account for vaccine failure and the increased persistence of clinical disease.

From 20 candidate genes of unknown function and that are highly up-regulated when *Bordetella* spp. is exposed to blood or serum, the gene that showed most promise was bsr. RB50Δbsr is a mutant of the *Bordetella* species *Bordetella bronchiseptica* strain RB450 with a deletion of the gene encoding for a small regulator. Results showed that the presence of this gene is required for persistence of *Bordetella bronchiseptica*, an established model organism for *B. pertussis*. In mice, RB50Δbsr was completely cleared from all organs, while wild type *B. bronchiseptica* colonized chronically. When studying the immune response, it was also detected that the strains evoked different immune responses, suggesting a difference in the adaptive immunity.

Bacterial strains and growth conditions. The strains used in this work are the wild type *Bordetella bronchiseptica* strain RB50, and a mutant strain that is a knock out for one of the regulators present in *Bordetellae*. This mutant is called RB50Δbsr (*Bordetella* Sigma Regulator). Bacteria were grown in Bordet-Gengou agar (Difco) supplemented with 5% sheep blood. Culture in liquid media was performed in Stainer-Scholte (SS) starting at optical densities of 0.1 or lower and grown overnight at 37 degrees and shaking (200 rpm).

Animal Experiments. C57Bl/6J mice (Jackson) were used for the time course infection. Mice were challenged intranasally with 50 μL of a bacterial suspension ($10^6$) under 5% isoflurane anesthesia. Mice were sacrificed at days 3, 7, 14, 21, 28, 35, 42, 49, and 56 post-challenge and harvested the organs. The killing was $CO_2$ followed by cervical dislocation. To test the role of adaptive immunity in the progression of the disease, B6.129S7-Rag1$^{TmMom}$/J mice were challenged with 50 mL of a bacterial suspension ($10^6$) and sacrificed them at 21 days postchallenge. Organs were harvested, and dilutions were plated on BGS agar. All plates were incubated for 48 hours at 37 degrees.

Immunology Assay. Mice were harvested at 21 days post-inoculation and their spleens and lungs were collected and processed. ACK-Lysing Buffer (Gibco for Life Technologies) was used to digest the erythrocytes and tryptan blue (COUNTESS™ cell counting chamber, V Invitrogen) was performed as previously described to count the total and live cells. To estimate granulocytes, B cell and T cells populations, and the assays were performed using standard protocols (Maecker et al., 2005, *BMC Immunology;* 6:13).

Results and Discussion

Papers have been published showing the role of different *Bordetella* sigma factors in siderophore formation or regulation of expression of Type 3 Secretion System. To study the role of bsr in *B. bronchiseptica*, a series of in vitro assays were performed to test duplication time and antibiotic susceptibility. No differences were found between wild type *Bordetella bronchiseptica* strain RB450 and the mutant RB50Δbsr in in vitro assays. In contrast, other mutants of sigma factors, such as the SigE mutant, fail to form a successful cell envelope stress response (Barchinger et al., 2012, *BMC Microbiology;* 12:179). This implies that this sigma factor plays an important role in evading immune response and other stressful situations such as temperature, antibiotic susceptibility, and others.

To further investigate the role of bsr (*Bordetella* Sigma Regulator) in colonization, persistence and outcome of the disease, a time course infection was performed using black mice C57Bl/6J and challenging them with 50 μL of a $10^6$ bacterial suspension (RB50 or RB50Δbsr). Mice were then harvested at different times and organs were plated in dilutions on BGS plates.

The results show that the mutant strain significantly decreases persistence in the lung. These results have great implications as this is the first virulent *Bordetella bronchiseptica* mutant that fails to persist in the nasal cavity of mice, indicating bsr is required for persistence in mice. The results showed that RB50Δbsr is nearly cleared from the lungs at day 14 post-inoculation while RB50 is cleared at nearly 50 days post-infection. The results also showed that RB50Δbsr is completely clear from nasal cavity at day 56 post-inoculation while the wild type strain RB50 is not clear even at 100 days post-inoculation. Previous papers have shown that RB54 fails to persist in nasal cavity, however this mutant is in Bvg– phase, which means that it is not expressing virulence factors (Harvill et al., 1999, *Infection and Immunity;* 67: 1493-1500). The bsr mutant expresses virulence factors, however, it fails to persist in these areas.

As discussed above, the mutant strain does not show differences in vitro. Moreover, in vivo, it is isolated in the same level as the wild type at the beginning of the infection (e.g., Day 3 post-inoculation), but it does not persist. This indicates that there are differences in the immune response generated by the wild type strain or the mutant, which results in clearance of infection in the mutant strain. To investigate the interactions with the immunity, cytokine production was studied in mice challenged with wild-type strain or the bsr mutant.

Spleens of the mice were collected at day 21 post-inoculation and processed. Flow cytometry was used to analyze the samples. The results showed that the number of cells and percentage of cells producing IL-17 is significantly higher in the mice challenged with RB50 (**95% confidence).

These results allow one to visualize precisely how these two strains interact differently with the immune response. Infecting mice with the bsr mutant led to a higher number of cells producing IL-10. This cytokine is associated with an anti-inflammatory immune response or Th-2. The mutant strain was cleared more rapidly from the organs due to it evoking robust host immune attack. In contrast, infecting mice with wildtype RB50 led to a higher percentage of cells producing IL-17. This cytokine is associated with chronic infection.

These results showed a novel interaction with the immunity leading one to ask if adaptive immunity is playing an important role in the clearance of bsr mutant. If the bsr mutant is cleared by a more robust immune response, then it should not be cleared more rapidly in mice lacking an adaptive immune response.

Figure 1B:
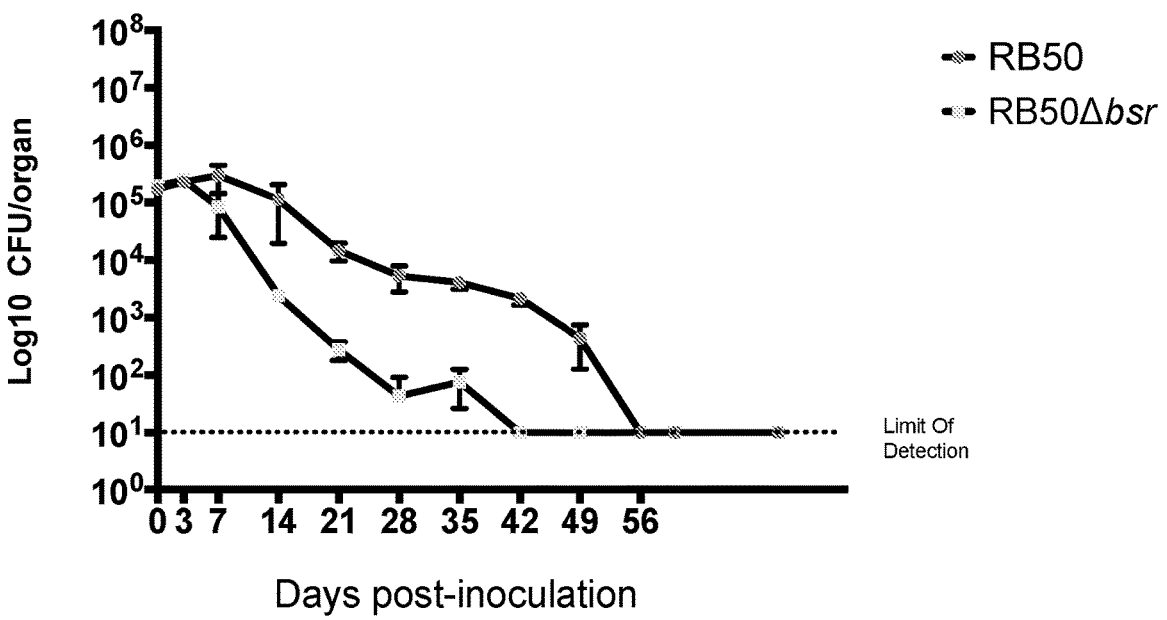

Because of the differences in clearance times from the lungs and the lack of persistence of the mutant in the nasal cavity, it was speculated that the mutant strain must be interacting differently with the adaptive immune response. To test this, immunocompromised mice, lacking in B and T cells, were challenged with the bsr mutant and the wildtype strain. If the bsr mutant in fact interacting with the adaptive immune response, then removing this line of defense should eliminate its defect. This is supported by the data. B6.129S7-Rag1$^{TmMom}$/J mice were challenged with 50 mL of $10^6$ bacteria. 21 days post-challenge the mice were sacrificed and organs were harvested and plated on BGS agar. The results showed that the numbers of CFU isolated from nasal cavity and trachea in mice challenged with both strains were similar. The fact that the mutant is defective in wild type mice but not in mice lacking B/T cells indicates that the bsr mutant was rapidly cleared by B and/or T cell-dependent mechanisms.

Conclusion

It can be concluded that bsr is required for persistence in mice. This can be seen by the early clearance of the bsr mutant from the lungs and its lack of persistence in the nasal cavity. Mice challenged with wild type RB50 induce higher production of IL-17 while mice challenge with the mutant strain produce more IL-10. Clearance of the mutant strain is mediated by B and T cells that are affected by such cytokines.

Example 3

B50Δbsr Confers Protection Against Colonization and Induces Long Lasting Immunity Bacterial strains and culture conditions. Bacteria were grown in Bordet-Gengou agar (Difco) supplemented with 10% sheep blood. Culture in liquid media was performed in Stainer-Scholte (SS) starting at optical densities OD600 of 0.1 or lower and grown overnight, shaking (220 rpm) at 37 C. Strains used in this study included strains of *B. bronchiseptica, B. pertussis* and *B. parapertussis* as well as some mutants.

Animal experiments. Wild type C57BL/6J mice were obtained from Jackson Laboratories, Bar Harbor, Me. All experiments were carried out in accordance with all institutional guidelines (AUP: A2016 02-010-Y2-A3) and following previously published protocols (Bendor et al., 2015, *PLoS One;* 10(10):e0140743; and Weyrich et al., 2012, *PLoS One;* 7(10):e45892). Briefly, the number of bacterial colony forming units in liquid cultures was calculated based on the optical density measured by absorbance of light at 600 nm. Bacteria were then diluted to $10^8$ CFU/ml in sterile PBS. After that, dilutions were made up to $10^5$ bacteria/mL. Plating dilutions on BGS agar and counting the resulting colonies after two days of growth at 37° C. Mice were sedated with 5% isoflurane (IsoFlo, Abbott Laboratories) in oxygen and 50 μl were inoculated intranasally.

Mice were euthanized with $CO_2$ inhalation followed by cervical dislocation on days 3, 7, 10, 14, 21, 28, 35, 42, 49, 56, 60, and 72 and respiratory tract and systemic organs, were extracted. Tissues were homogenized in PBS, serially diluted and plated onto BG agar plates with 200 μg/mL streptomycin, and colonies were counted after 2 days of growth at 37° C. for *B. bronchiseptica* and 4 days for *B. pertussis* or *B. parapertussis.*

For the vaccination study, 1:5 dilution of Adacel (Sanofi Pasteur) was prepared. Mice were injected intraperitoneally with 500 μL of the vaccine dilution. For the controls of this experiment, PBS was intraperitoneally injected in the same conditions and volumes as the vaccinated group. Vaccinated group and PBS control were boosted at 14 days following the same protocol. The third group were mice challenged as previously described with RB50Δbsr. 60 days later, mice were challenged intranasally with 50 μL of PBS containing $10^5$ bacteria of *B. bronchiseptica* RB50; *B. pertussis* Tohama I; or *B. parapertussis* 12829. Mice were harvest 7 days post-challenge. Other controls used included: 1) mice challenged with RB50Δbsr and harvest 60 days after challenge to confirm complete clearance from all mice organs; and 2) mice infected with RB50Δbsr kept with no second challenge until the end of the experiment to control clearance and cross-contamination.

For the passive transfer experiments, injection of 200 μl of immune serum intraperitoneal into naive mice was immediately followed by intranasal inoculation. Animals were sacrificed on the indicated day post-transfer and inoculation and colonization determined as described.

Animals were handled following institutional guidelines, in keeping with full accreditation from the Association for Assessment and Accreditation of Laboratory Animal Care International.

Flow cytometer. Spleen and lung were collected to study cells number and cytokine production. Spleen was collected from the mouse and homogenized and passed through the cell strainer. Number of total cells and live cells was assessed with the hemocytometer and using the tryptan blue stain as previously described. $20\times10^6$ live cells were plated in a 96 well plate for staining following the protocols recommended by the manufacture.

Previously published protocols were followed to obtain cells from lung. Number of total cells and live cells was assessed with the hemocytometer and using the tryptan blue stain as previously described. $10\times10^6$ live cells were plated in a 96 well plate for staining. For the staining, previously reported methods were followed.

Ethics Statement. This study was carried out in strict accordance with the recommendations in the Guide for the Care and Use of Laboratory Animals of the National Institutes of Health. The protocol was approved by the Institutional Animal Care and Use Committee at University of Georgia, Athens (A2016 02-010-Y2-A3 *Bordetella*-Host Interactions). All animals were anesthetized using 5% isoflourane and euthanized using carbon dioxide inhalation followed by cervical dislocation to minimize animal suffering.

Results bsr is required to persist in respiratory tract. To determine whether bsr is important in the interaction with the host, a time course infection was performed using C57Bl/6J mice from Jackson. 50 μL of $10^5$ bacterial suspension in PBS, were inoculated intra-nasally and groups of 4 mice were euthanized at different time points. These results are shown in FIGS. 1A-1C.

The results showed that RB50Δbsr fails to persist in middle and low respiratory tract. Mice challenged with RB50 clear trachea by day 56, while mice challenged with RB50Δbsr clear trachea by day 42 (FIG. 1B). Importantly, this difference is most impressive when studying lungs, and RB50 clears at day 56 while RB50 Δbsr clears at day 14; which means that infection is clear in the lower respiratory tract, 42 days in advance when challenge with RB50Δbsr (FIG. 1A).

Figure 1C:
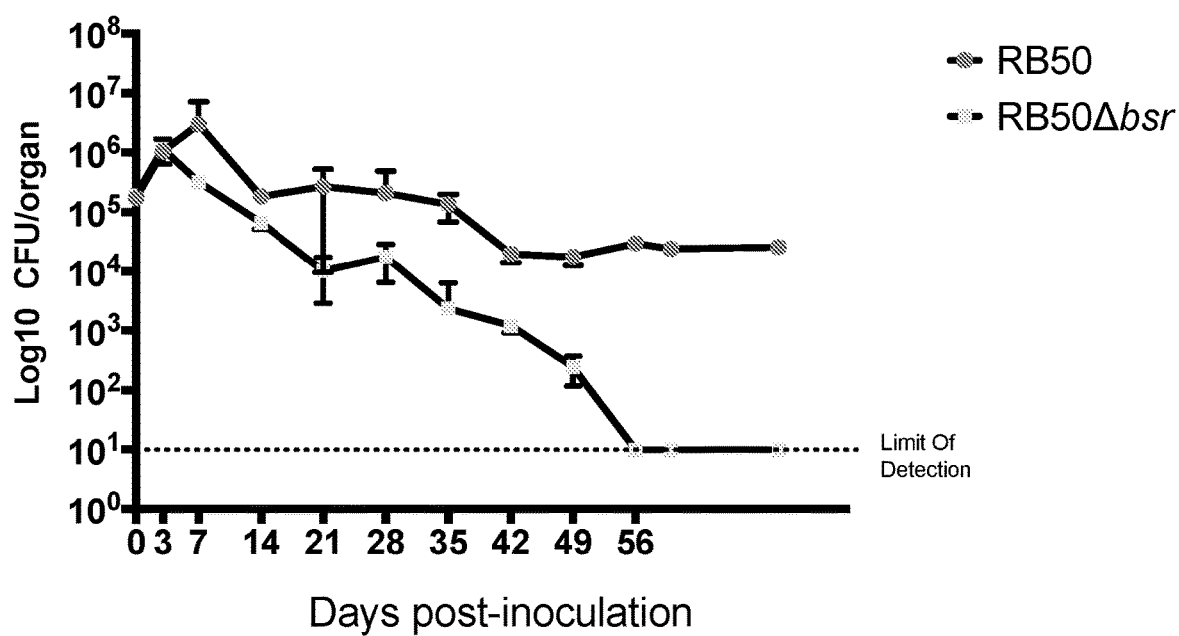

Importantly, the results showed that RB50Δbsr is also cleared from the nasal cavity by day 56 post-infection (FIG. 1C). No mutant that initially colonized mice has been observed to be later cleared by adaptive immunity. The only mutant reported to fail in persistence was one that failed to colonize mice altogether, Bvg− phase locked mutant which is a-virulent (Harvill et al., 1999, Infect Immun; 67(3):1493-500). This is the first report of a Bvg+ mutant strain that is able to colonize the host efficiently but is completely cleared from nasal cavity.

All together these results indicate that RB50Δbsr fails to persist in respiratory tract, and excitingly it is completely cleared from nasal cavity 56 days post-inoculation.

Figure 2A:
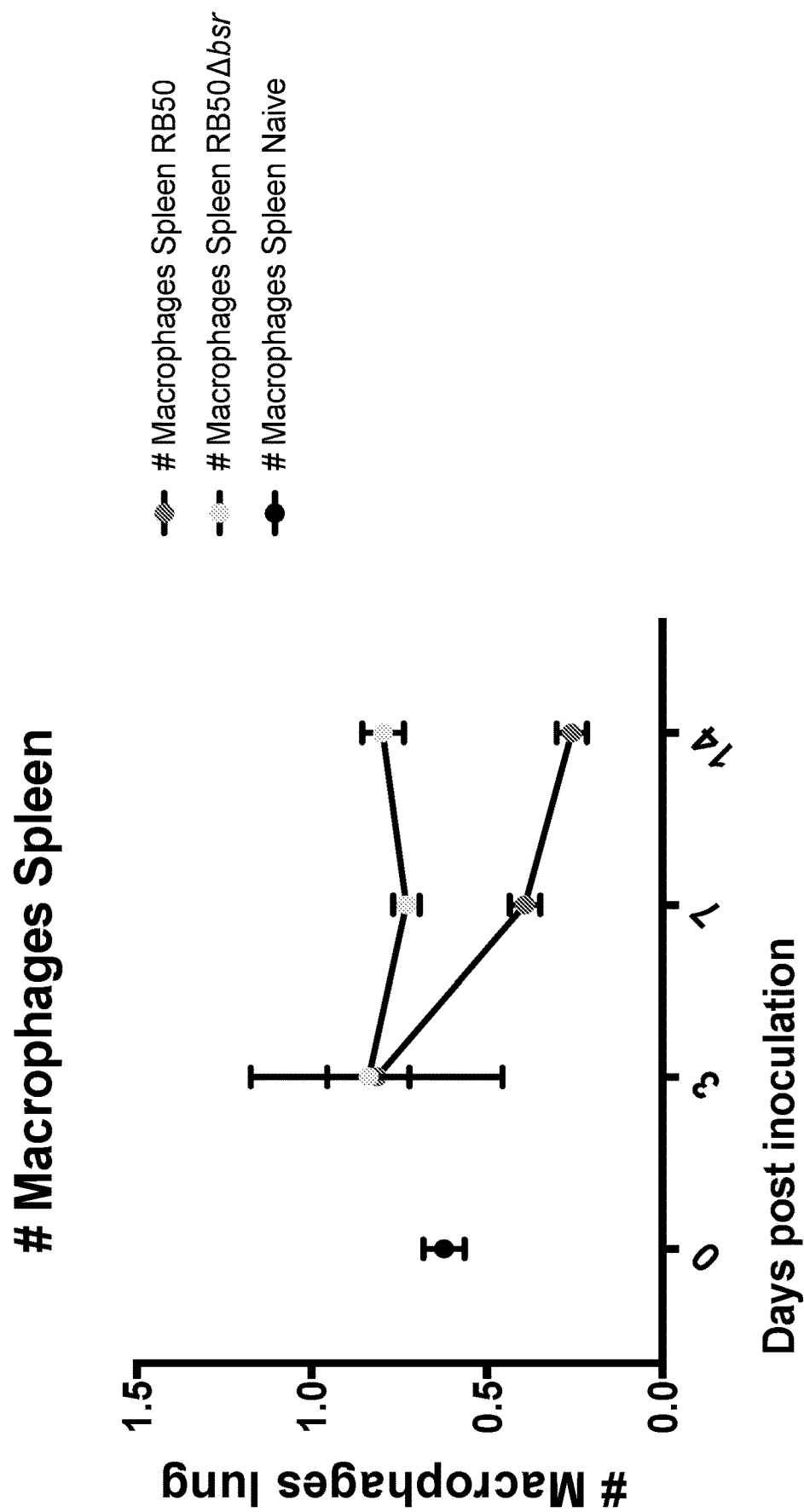
Figure 2B:
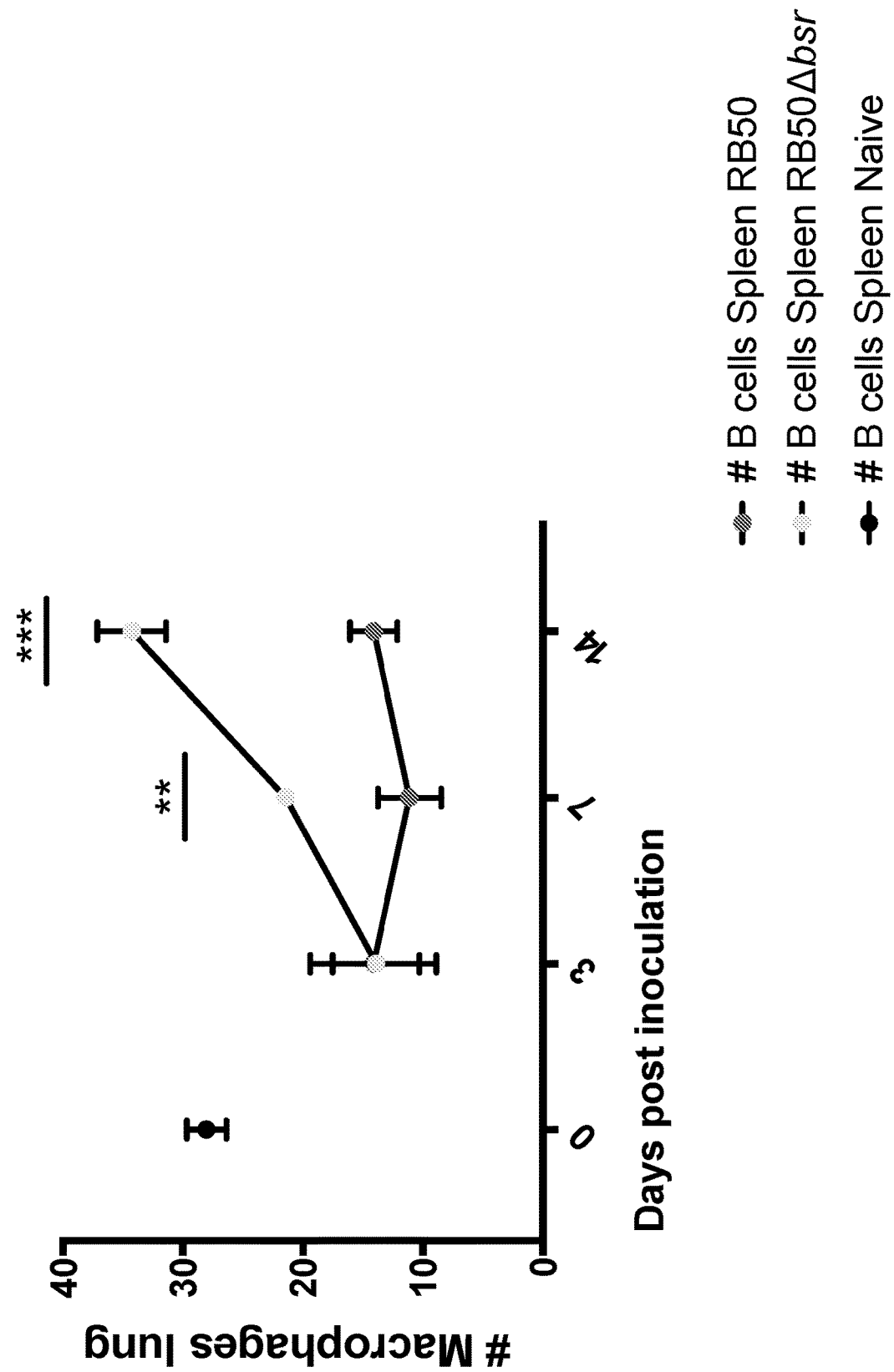

To determine whether bsr is important in the interaction with the host immunity, a time course infection was performed using C57Bl/6J mice from Jackson. 50 µL of $10^5$ bacterial suspension in PBS, were inoculated intra-nasally and groups of 4 mice were euthanized at different time points to analyze immune cells count in lungs and spleen as well as some cytokines (FIG. 2A-2C).

These results indicate that RB50Δbsr induces a more robust and earlier immune response than RB50. The numbers of T cells, CD4, macrophages and B cells where higher in spleen for those mice challenged with RB50Δbsr; while the numbers of CD4, CD8, macrophages, neutrophils and B cells where higher on lungs for those mice challenged with RB50Δbsr than in those challenged with wild type RB50.

Interestingly neutrophil recruitment was higher in the mice challenged with RB50Δbsr in day 3 and 7; but by day 14 the value is similar to those mice challenged with RB50. Similarly, macrophages numbers where high in spleen and lung of the mice challenge with RB50Δbsr.

Further, the number of CD4 and B cells was significantly higher in the mouse challenged with the mutant strain (RB50Δbsr) indicating that this might confer protective immunity against other Bordetella strains. It has been previously reported that CD4 and B cells are required for a protective immunity against B. pertussis (Leef et al., 2000, J Exp Med; 191(11):1841-52).

This example also found the CD8 number was high in lungs. It has been previously reported that CD8 promote protective immunity to respiratory infection with B. pertussis (Dunne et al., 2009, J Immunol; 183(1):400-10). All these data together indicate that challenge with RB50Δbsr induces a higher and more robust immune response. Thus, it is likely that RB50Δbsr can confer protection against further encounters with other Bordetella spp.

RB50Δbsr induces more diverse and robust antibody response. To determine whether RB50Δbsr induces a high antibody response, the antigenic profile of RB50 versus RB50Δbsr was compared using as primary antibodies serum from mice challenged with RB50 or RB50Δbsr. The results showed that RB50Δbsr induces the production of novel antibodies that do not appear in RB50 or when incubating with the serum of mice challenged with RB50. This indicates that there is production of completely novel antibodies after challenge with RB50Δbsr.

Figure 3B:
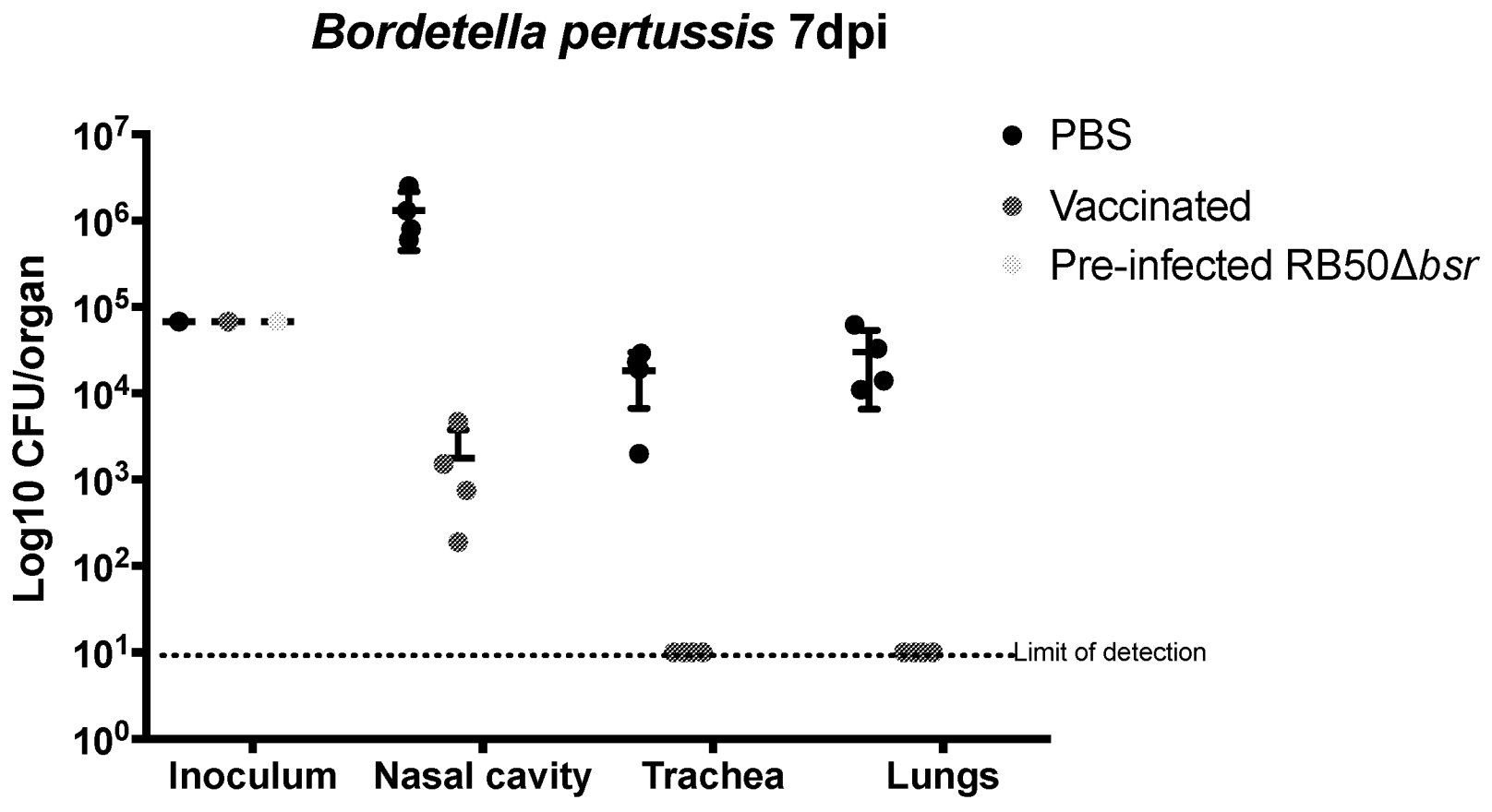

As shown in FIG. 3A-3C, RB50Δbsr confers sterilizing immunity against all classical Bordetellae. To determine whether RB50Δbsr confers protection against further Bordetellae infection; 3 groups of mice where or vaccinated and boosted with ½₀ dose of Adacel, challenged with RB50Δbsr or controls (intraperitoneal PBS). 60 days later, three 3 mice that were challenged with RB50Δbsr were euthanized to confirm clearance from nasal cavity and rest of the organs. The next step was to challenge groups of 4 mice of each condition with B. bronchiseptica RB50, B. pertussis Tohama I or B. parapertussis 12829. Seven days post-challenge, mice were euthanized, and organs were harvested to enumerate CFUs. As shown in FIGS. 3A-3C, Adacel vaccination protects from disease and colonization of the lungs and trachea, however it allows for colonization of the nasal cavity, as previously described (Gaillard et al., 2014, Vaccine; 32(8):931-7; Smallridge et al., 2014, J Infect Dis; 209(12):1981-8; and Goebel et al., 2009, PLoS One; 4(8): e6778). However, previous challenge with RB50Δbsr induced sterilizing immunity against further infection with any of the 3 classical Bordetellae. Following the same experimental setting, we infected with clinical strains of B. pertussis, B. parapertussis and B. bronchiseptica. Our results indicate that we can provide sterilizing immunity against multiple strains of B. pertussis and B. parapertussis (including BPPS which is ovine). In addition, prior exposure to the bsr mutant successfully conferred sterilizing immunity of trachea and lungs against multiple B. bronchiseptica strains and significantly reduced the levels of colonization in the nasal cavity.

Figure 4A:
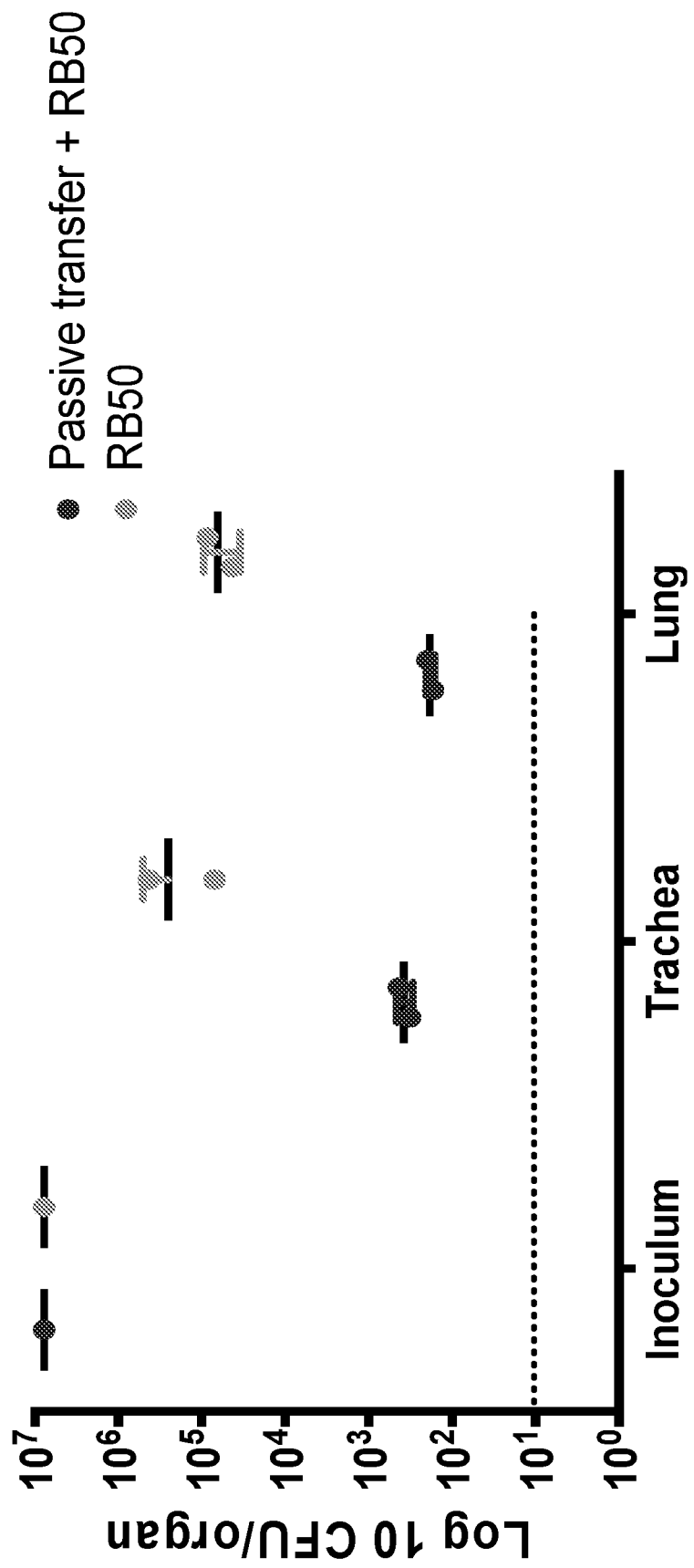
FIGS. 4A and 4B. RB50Δbsr induces antibody protection even with lower dosages of inoculum. C57BL/6J mice were intranasally inoculated with 50 μL of 5×10$^7$ bacteria either RB50 or RB50Δbsr. Mice were harvest at 28 days and serum was collected. 150 μL of serum was IP injected in naïve animals versus PBS as control. Three hours later mice were intranasally challenged with RB50 or BP536. Three days post-inoculation, mice were harvest and organs plated in BGS.
Figure 4B:
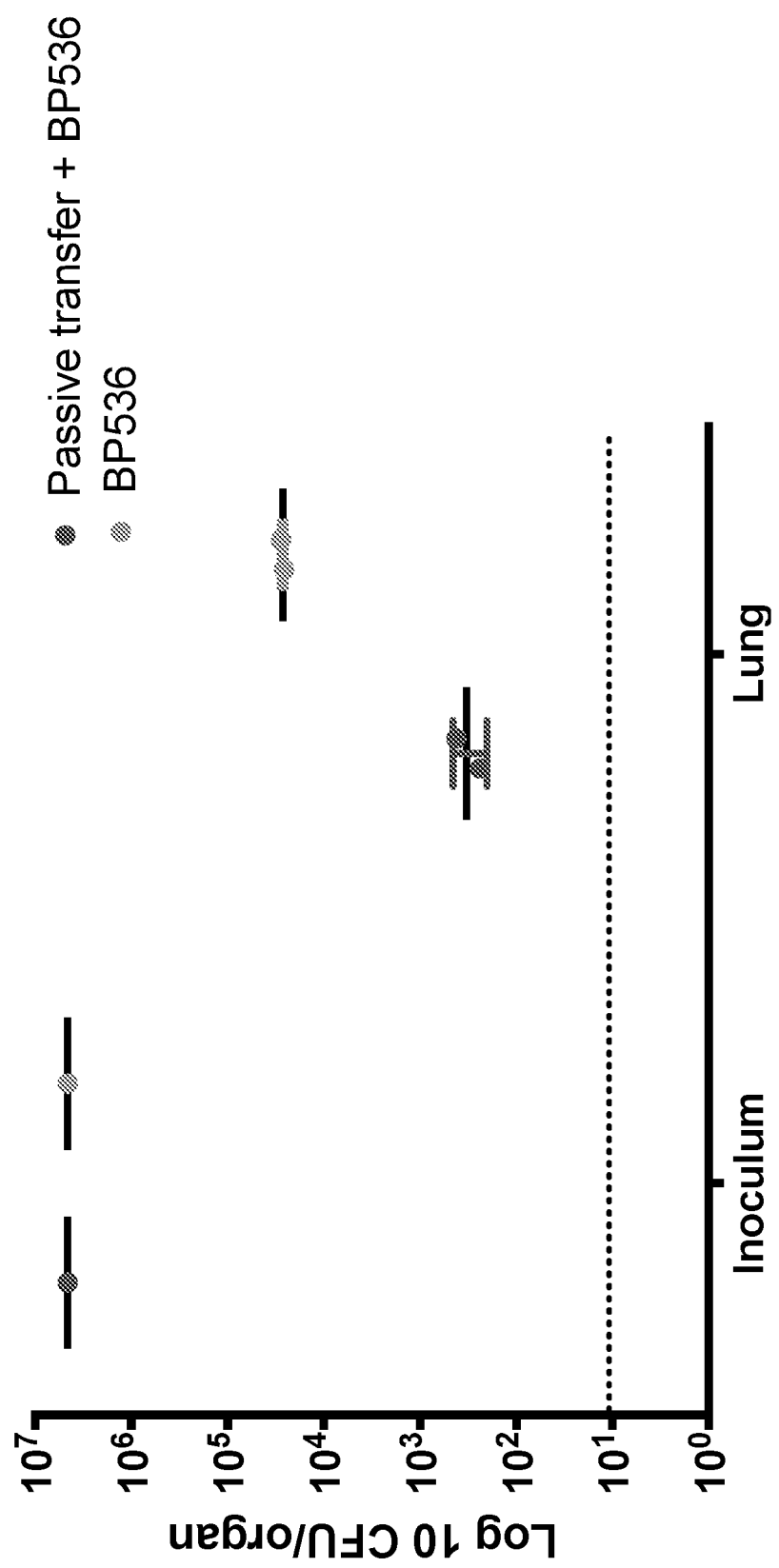

To further investigate if this protection is conferred by antibodies, passive transfer of antibodies from mice challenged with RB50Δbsr was performed. Intraperitoneal injection of 150 µL of serum was performed and 3 hours later mice were challenged with either B. bronchiseptica RB50 or B. pertussis Tohama I. Mice were sacrificed 3 days post-challenge and organs were harvested to enumerate CFUs. As shown in FIG. 4A and FIG. 4B, passive transfer of serum from mice challenged with RB50Δbsr decreased the number of colonies in the lung by 99.9%.

To further investigate if smaller dosages will also confer protection, SCFU of RB50Δbsr was tested to determine if it will confer protection against further encounters with Bordetella spp. Groups of 4 mice were challenged with 5 µl of PBS containing SCFU of RB50Δbsr, 60 days after each group was re-challenge with 50 µL of PBS containing 5×$10^5$ Bordetella spp. 7 days later, mice were euthanized, and organs were harvest and plated on BGS. The results show that full protection is conferred against B. bronchiseptica and B. parapertussis in the trachea and lungs. Low levels of colonization of nasal cavity indicating that although really low dosages confer broad and strong protection, more studies need to be done to determine the lowest dosage at which complete sterilizing immunity is conferred.

Antibody production in TLR4 deficient mice was further explored. LPS is one of the most antigenic components of Bordetella spp. RB50Δbsr generates a robust antibody response independent of LPS recognition. Results showed that at day 10 TLR4 deficient mice generate a robust antibody response with antibody titers that are approximately 20,000 as early as day 10 post-inoculation. On the other hand, mice challenge with RB50 had no detectable antibodies on day 10 post-inoculation. RB50 did not induce comparable antibody titer until day 21 post-infection, indicating that bsr mediates a substantial delay in the generation of antibodies in these mice. Similarly, in C57BL/6J wild-type mice, the antibody titers induced by RB50Δbsr spike at day 7 post-infection, but mice infected with RB50 do not make detectable antibodies at this early time point.

Example 4

Immunomodulation Suppresses Adaptive Immunity to *Bordetella* Infection

To successfully persist in the face of the many antimicrobial weapons of the host immune system, pathogens must either defend against them or disrupt their expression. Classical *Bordetellae* are very closely related subspecies that are known to immunomodulate as an aspect of their successful strategies allowing them to either persist for life (*B. bronchiseptica*) or induce highly fulminant disease, facilitating rapid transmission and repeated infection (*B. pertussis*). Exploring the hypothesis that conditions signaling engagement with immune cells would induce important immunomodulatory mechanisms, a putative regulator implicated in their control was identified. Deleting it did not affect colonization of the host but profoundly affected the generation of adaptive immune response, conferring robust sterilizing immunity against reinfection with all Classical *Bordetella* species. These finding both reveal new bacterial immunomodulatory abilities and demonstrate that disrupting regulators of immunomodulatory pathways can lead to better protective immunity than vaccines or natural infection.

Introduction

Host immunity has evolved into a sophisticated array of mechanisms that attempt to maintain the host in a homeostatic "healthy" state. A central feature of host immune response is the dynamic surveillance systems of innate immunity that coordinate an antimicrobial response particular to the set of pathogen associated molecular patterns (PAMPs) detected by the aggregate set of pattern recognition receptors (PRRs). The combination of PRR and other signals received by immune cells at or near the site of infection can have a profound effect on the generation of protective immunity.

To evade these robust antimicrobial defenses, many microorganisms have developed sophisticated mechanisms to modulate the immune responses in order to persist, efficiently transmit to other hosts and subsequently re-infect the same host (Nicholson et al., 2014, *Infect Immun;* 82:1092-1103; Buboltz et al., 2009, *Infect Immun;* 77:3969-3977; Fennelly et al., 2008, *Infect Immun;* 76:1257-1266; Skinner et al., 2004, *J Immunol;* 173:1934-1940; Stockbauer et al., *Cell Microbiol;* 5:123-132; Perez Vidakovics et al., 2006, *FEMS Immunol Med Microbiol;* 48:140-147; Ross et al., 2004, *Infect Immun;* 72:1568-1579; Dadaglio et al., *J Immunol;* 193:1787-1798; Pilione and Harvill, 2006, *Infect Immun;* 74:1043-1049; Gorgojo et al., 2017, *PLoS One;* 12:e0169936; Skinner et al., 2005, *J Immunol;* 175:4647-4652; Dewan et al., 2017, *J Infect Dis;* 216:899-906; Liu et al., 2012, *Mucosal Immunol;* 5:320-331; Liu et al., 2011, *Front Microbiol;* 2:52; Liu et al., 2014, *Mucosal Immunol;* 7:165-176; VanCott et al., 1998, *Nat Med;* 4:1247-1252; and Azuma, 2006, *J Periodontal Res;* 41:361-373). There is growing evidence that bacteria can sense many cues of aspects of the host response, allowing them to evade or subvert immunity. We reasoned that to optimally manipulate the host response a successful persistent pathogen might sense cues associated with contact with host immune cells and respond with increased expression of key immunomodulators.

The *Bordetella*-mouse experimental system provides an optimal model in which to study specific aspects of bacterial-host immunomodulation (Pilione and Harvill, 2006, *Infect Immun;* 74:1043-1049; Dewan et al., 2017, *J Infect Dis;* 216:899-906; Pishko et al., 2004, *Eur J Immunol;* 34:184-193; Preston et al., 2003, *Mol Microbiol;* 48:725-736; Goebel et al., 2009, *PLoS One;* 4:e6778; and Kirimanjeswara et al., 2005, *J Immunol;* 175:7504-7511). The genus *Bordetella* comprises several closely related organisms (*B. bronchiseptica, B. pertussis*, and *B. parapertussis*) causing respiratory diseases that can either be acute, persistent or chronic, demonstrating that these species effectively modulate immunity in robust but poorly understood ways (Perez Vidakovics et al., 2006, *FEMS Immunol Med Microbiol;* 48:140-147; Ross et al., 2004, *Infect Immun;* 72:1568-1579; Pilione and Harvill, 2006, *Infect Immun;* 74:1043-1049; Gorgojo et al., 2017, *PLoS One;* 12:e0169936; Skinner et al., 2005, *J Immunol;* 175:4647-4652 Kirimanjeswara et al., 2005, *J Immunol;* 175:7504-7511; Gorgojo et al., 2012, *Infect Immun;* 80:4309-4316; Wolfe et al., 2010, *J Immunol;* 184:1392-1400; Thakar et al., 2007, *PLoS Comput Biol;* 3:e109; Yuk et al., 2000, *Mol Microbiol;* 35:991-1004; Kirimanjeswara et al., 2005, *J Clin Invest;* 115:3594-3601; Bendor et al., 2015, *PLoS One;* 10:e0140743; Weyrich et al., 2012, *PLoS One;* 7:e45892; Hickey et al., 2008, *J Leukoc Biol;* 84:234-243; Siciliano et al., 2006, *J Immunol;* 177: 7131-7138; Perkins et al., 2007, *Mol Microbiol;* 66:1003-1015; Cerny et al., 2015, *J Immunol;* 194:4901-4913; and Hasan et al., 2018, *Infect Immun;* 86(3):pii: e00445-17).

Since *B. bronchiseptica* and other *Bordetella* species naturally and highly efficiently infect mice, the details of their immunomodulatory functions can be studied in the context of natural infection. *B. bronchiseptica* can persist for life in the airways of healthy mice, but fulminant infection can expose them to extensive inflammation, with its many antimicrobial challenges. Exposure to such immune cells also presents the opportunity to modulate innate and adaptive immunity. Reasoning that well adapted pathogens like the *Bordetellae* should have evolved a response to such challenges/opportunities, we recently examined their response to exposure to blood or serum, as markers of inflammation and/or of lymphoid organs. This example demonstrates that all three classical *Bordetella* species respond to exposure to blood or serum by inducing the expression of several known immunomodulators, as well as many uncharacterized genes.

Amongst the blood- and serum-induced genes was an apparent sigma factor previously referred to as btrS or bprL and shown to regulate the type III secretion system. This analysis implicated this gene in broader regulation of immunomodulatory functions. Deleting btrS did not affect the efficient colonization and growth within the respiratory tract of its host but resulted in a dramatically increased immune response that was able to completely clear infection. The mutant induced much more robust recruitment into the lungs of B and T cells that are required for its clearance. Wild-type mice convalescent from infection with the mutant were protected from colonization by *B. bronchiseptica, B. pertussis*, or *B. parapertussis*. The sterilizing immunity to all three pathogens is substantially stronger and more complete than that conferred by current vaccines, indicating that better protection can be attained. Understanding the immunomodulatory mechanisms involved in these effects are likely to allow dramatic improvements in treatments and vaccines, which are desperately needed.

Materials and Methods

Bacterial strains and culture conditions. Bacteria were grown in plates of Bordet-Gengou agar (Difco) supplemented with 10% sheep defibrinated blood and 200 µg/mL of streptomycin (Gestal et al., 2018, *Front Microbiol;* 9:1969). Strains used in this study are the same strains of *B. bronchiseptica, B. pertussis,* and *B. parapertussis* used are as previously published (Gestal et al., 2018, *Front Microbiol;* 9:1969). Knock out mutants were generated as previously described (Dewan et al., 2017, *J Infect Dis;* 216:899-906; Bendor et al., 2015, *PLoS One;* 10:e0140743; Barchinger et al., 2012, *BMC Microbiol;* 12:179; Zhang et al., 2009, *PLoS One;* 4:e6989; and Pilione et al., 2004, *Infect Immun;* 72:2837-2842).

Enzyme-linked immunosorbent assays. 96-well microtiter plates (Costar) were coated with heat-killed *B. bronchiseptica* or the mutant and incubated in a humidified chamber at 35° C. for four hours, then blocked with PBST and 1% BSA and left overnight at 40° C. Assays were performed according to previously published protocol (Hester et al., 2012, *PLoS One;* 7:e47635). Superblue was added to start the reaction, which was terminated with HCL after ten minutes. The plates were read at an OD of 450 nm. The titer was determined to be the reciprocal of the lowest dilution greater than zero.

Animal experiments. Wild-type C57BL/6J and Rag−/− (B6.129S7 Rag1tm1Mom/J) mice were obtained from Jackson Laboratories, Bar Harbor, Me. or our breeding colony (established from Jackson laboratories mice). Mice were bred and maintained at Coverdell Building, University of Georgia, Ga., (AUP: A2016 02-010-Y2-A3) (Preston et al., 2003, *Mol Microbiol;* 48:725-736; and Kirimanjeswara et al., 2005, *J Immunol;* 175:7504-7511). All experiments were carried out in accordance with all institutional guidelines (*Bordetella* Host Interactions AUP: A2016 02-010-Y2-A6) and following previously published protocols to enumerate CFUs (Dewan et al., 2017, *J Infect Dis;* 216:899-906; Hester et al., 2015, *PLoS One;* 10:e0130964; Weyrich et al., 2014, *J Infect Dis;* 209:913-921; and Taylor-Mulneix et al., 2017, *PloS Blob;* 15: e2000420), passive transfer studies (Kirimanjeswara et al., 2005, *J Immunol;* 175:7504-7511; Zhang et al., 2009, *Infect Immun;* 77:5050-5058; Wolfe et al., 2005, *Infect Immun;* 73:6508-6513; and Leef et al., 2000, *J Exp Med;* 191:1841-1852) and vaccination studies (Smallridge et al., 2014, *J Infect Dis,* 209: 1981-1988). All results were graph in GraphPrism and statistical significance was calculated using two-way ANOVA.

Flow cytometry. Spleen and lungs were processed and stained as previously described (Boehm et al., 2018, *Infect Immun;* 86(10):pii: e00857-17). For staining, previously reported methods were followed (Halim and Takei, 2014, *Current Protocols in Immunology;* 3.25:1-13 (Wiley online library); and Rolin, et al., 2014, *PLoS One;* 9:e85229) using commercially available antibodies. The acquisition of the data was performed in FACS and analysis was performed with FlowJo 10.0 following standard gating strategy. Statistical significance was calculated using two-way ANOVA in GraphPrism.

Histopathology. Mice tissue was process as previously reported (McHale et al., 2018, *J Vet Diagn Invest;* 30:260-262; and McKeithen et al., 2017, *PLoS One;* 12:e0188643). The heads were decalcified in Kristensen's solution and sectioned through the nose, brain, and ear. Tissues were subsequently processed and stained with hematoxylin and eosin. A board-certified pathologist performed blindly all microscopic evaluations of these HE-stained sections at the AVDL. The codes and abbreviations used as entries in these tables are explained at the bottom of each table.

Ethics Statement. This study was carried out in strict accordance with the recommendations in the Guide for the Care and Use of Laboratory Animals of the National Institutes of Health. The protocol was approved by the Institutional Animal Care and Use Committee at the University of Georgia, Athens (A2016 02-010-Y2-A3 *Bordetella*-Host Interactions and A2016 07-006-Y2-A5 Breeding protocol). All animals were anesthetized using 5% isoflurane and euthanized using carbon dioxide inhalation followed by cervical dislocation to minimize animal suffering. Animals were handled following institutional guidelines, in keeping with full accreditation from the Association for Assessment and Accreditation of Laboratory Animal Care International.

Results btrS is implicated in immunomodulation. We have hypothesized that *Bordetellae* can detect signals in blood/serum and respond with their most potent immunomodulatory functions. Our recent description of sets of genes induced by blood and serum allowed us to search this set for key regulators of unknown mechanisms of immunomodulation. Using a STRING analysis, we identified a network of induced genes that are linked in a variety of ways that suggest coordinated functions, including genomic proximity, co-expression under various conditions, etc.

This analysis revealed a network with nodes of particular interest for their connections to many other factors, some of which are known to be involved in complex interactions with the host. This analysis revealed a particularly intriguing and well-connected gene named brpL/btrS that is known to be involved in regulation of important immunomodulators, including the Type 3 Secretion System, important virulence regulators such as hfq or sigE (RpoE), iron and heme sensors and transporters and other unknown proteins. These analyses led us to consider btrS as a potential key regulator of immunomodulatory functions. To further support our hypothesis, we observed this gene is up-regulated 2.5 folds when *B. bronchiseptica* is internalized in macrophages but not when internalized in the amoeba *Dyctiostelium discoideum*. This evidence that btrS responds to signals associated with contact with immune cells and is connected in various ways to known immunomodulators suggested it may be a key regulator of known and novel immunomodulatory mechanisms.

btrS is required for respiratory tract persistence. To investigate the role of btrS in multiple aspects of colonization, growth, persistence and pathogenesis, we generated a clean, in-frame deletion of the btrS gene in the *B. bronchiseptica* strain RB50, following previously established protocols (Harvill et al., 1999, *Infect Immun;* 67: 1493-1500). The construction was verified by PCR and whole genome sequencing. No differences in growth rate in laboratory media, hemolytic activity, or survival in serum were observed between wild-type and the mutant strain.

To examine the effects of this mutation in vivo, we evaluated the course of infection in wild-type C57Bl/6J mice (FIG. 1A-1C). Both RB50 and the mutant (RB50ΔbtrS) colonized and grew efficiently in the lower respiratory tract (LRT) during the first few days of infection, inducing similar modest inflammation. But after about a week the mutant began to demonstrate profound defects. Wild-type bacteria persisted in the lungs up to 56 days, whereas the mutant was nearly cleared by day 14 and was absent on day 21 and every day thereafter. Even more striking was the phenotype of the mutant in the nasal cavity. Wild-type *B. bronchiseptica* persisted in the nasal cavity of mice for at least 56 days in this experiment and consistently persisted for life in all previous experiments (Barchinger et al., 2012, *BMC Microbiol;* 12:179). In contrast, the btrS mutant was completely cleared from the nasal cavity by day 56. This is the first *B. bronchiseptica* mutant described that efficiently colonizes and grows within mice but is completely cleared from the upper and lower respiratory tract. The timing of this clearance coincided with the timing of the generation of early B and T cell responses, suggesting a dramatically different interaction with adaptive immunity that allows for the generation of more effective protection.

Clearance requires adaptive immunity. To investigate if clearance of RB50ΔbtrS is mediated by adaptive immunity, we challenged Rag−/− mice, which are deficient in B and T cells. Sets of 4 mice were inoculated with either wild-type or the ΔbtrS mutant and euthanized 21 days later. Both, wild-type and mutant strains were recovered in similar numbers from all organs of the respiratory tract, indicating that RB50ΔbtrS is not defective in the absence of B and T cells and supporting the hypothesis that its rapid and complete clearance is T/B cell-mediated.

Figure 6A:
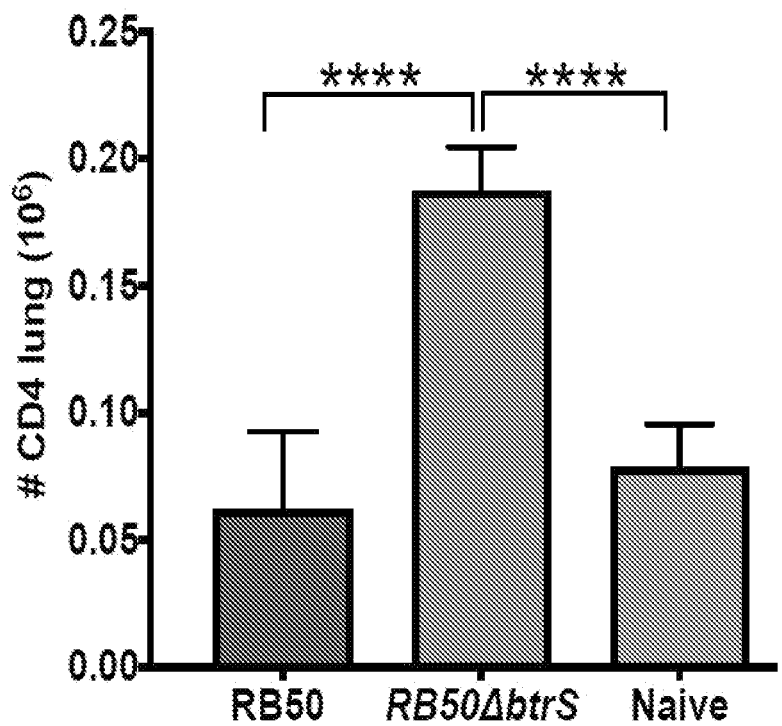
FIGS. 6A and 6B. BtrS down-regulates T cell recruitment to lungs. In blue is represented RB50 wild-type strain of *B. bronchiseptica* and in red the strain RB50ΔbtrS mutant and in grey the mock control (uninfected group). The black boxes indicate significant differences between treatments. Statistical difference was determine using Two-Way Anova test *=p<0.001 and **=p<0.0001.
Figure 6B:
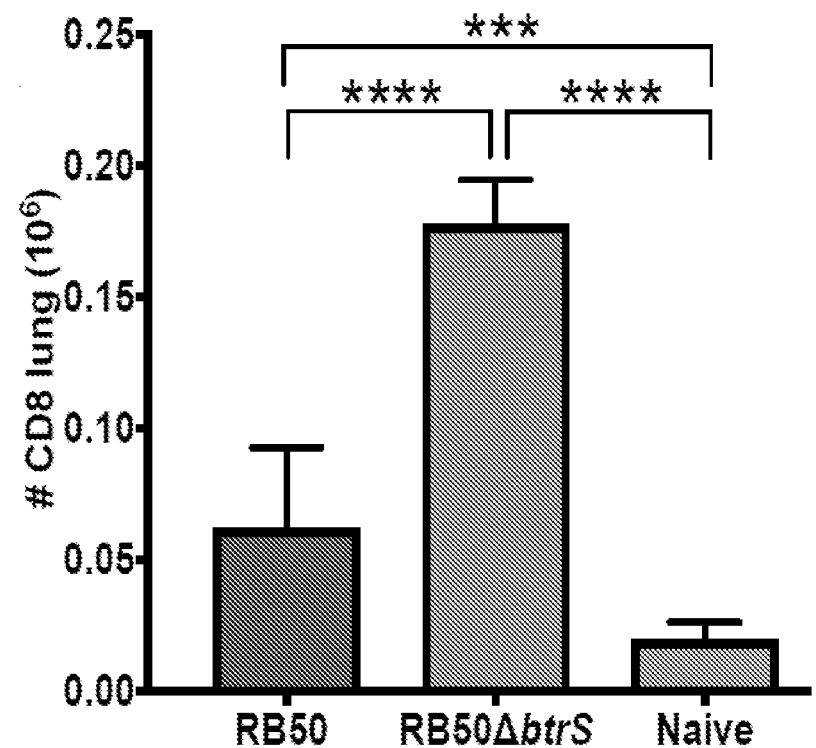
Figure 7A:
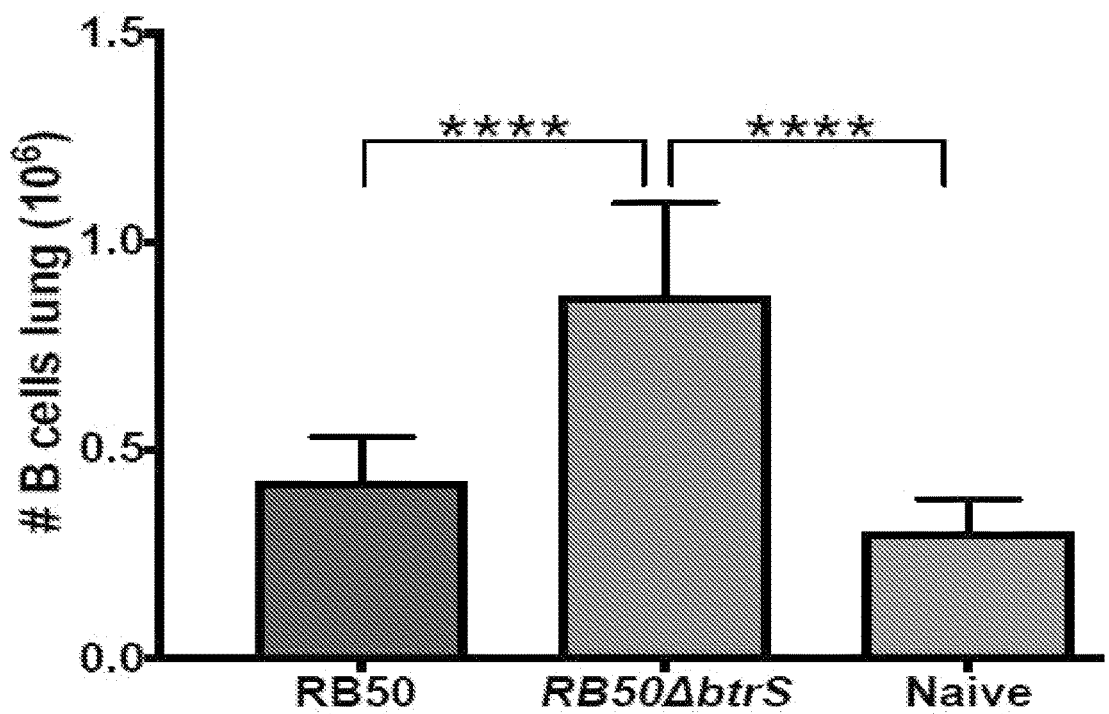
FIGS. 7A-7C. btrS down-regulates B cell recruitment in lungs. The black boxes indicate significant differences between treatments. Statistical difference was determine using Two-Way Anova test ****=p<0.0001 or *=p<0.1.
Figure 7B:
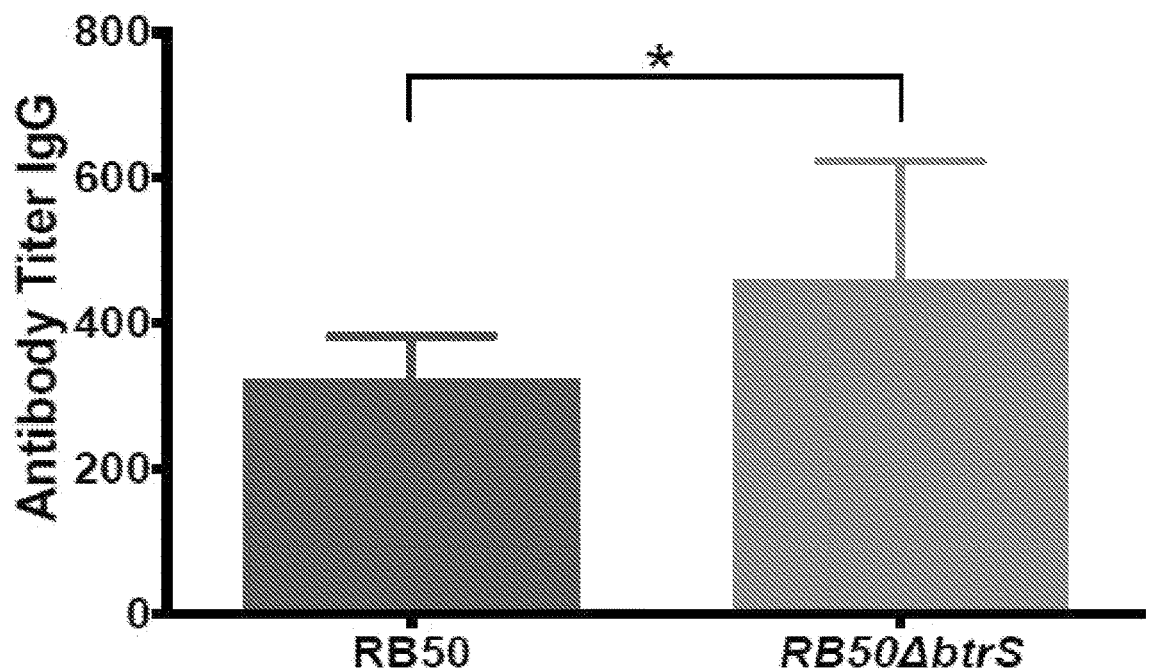
Figure 7C:
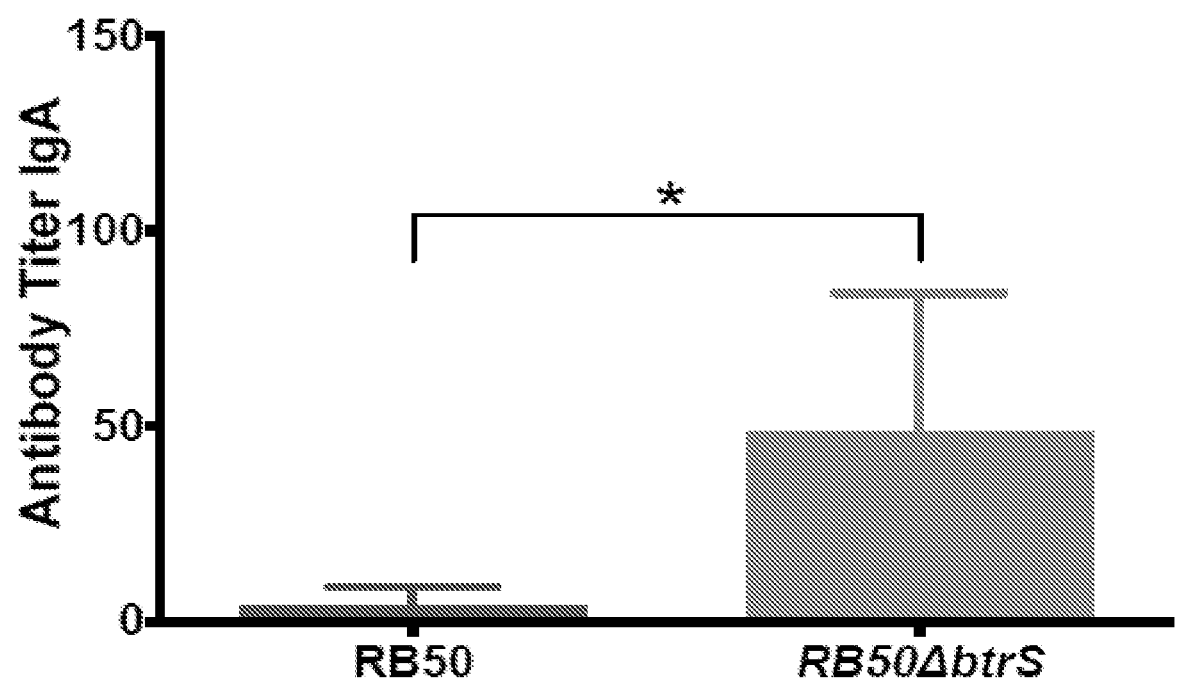

To investigate the possibility that these striking results were somehow dependent on the unnaturally large inoculum, overcoming the remnant immune functions in these immunodeficient animals, a second challenge was performed in which mice were intranasally inoculated with 5 µl of PBS containing 100 bacteria. 24 days later RB50 and RB50ΔbtrS were both recovered in similarly high numbers, indicating that the mutant is not defective in any of the functions necessary for colonization, growth and spread to lower respiratory tract, although it is recovered in somewhat lower numbers in the nasal cavity (FIG. 5). The observations that btrS is required for persistence in wild-type mice but does not affect infection and persistence in trachea and lungs of Rag−/− mice indicates that btrS is involved in the disruption of a robust host adaptive immune response that, in its absence, is able to completely clear this notoriously persistent bacteria.

btrS down-regulates T cell recruitment to lungs. To investigate potentially different roles of T cells in the control of wild-type and clearance of the btrS mutant, we analyzed via flow cytometry the T cell populations present in the lungs 14 days post-inoculation with each. Wild type RB50 did not increase CD4+ T cell numbers in the lungs but did significantly increase CD8+ T cells over the non-infected control (FIGS. 6A and 6B). Interestingly, challenge with RB50ΔbtrS significantly increased recruitment of both CD4+ and CD8+ T cells. It is important to highlight that at this time point (day 14) the ΔbtrS induces much greater T cell response even though it is present at roughly ¹⁄₁₀₀₀ the numbers of the wild type. Conversely, the wild type bacteria, via mechanisms that require btrS, substantially block T cell responses while growing and persisting at high numbers in the lungs.

btrS down-regulates B cell recruitment. To examine the role of B cells in the rapid clearance of the mutant, we analyzed the B cell populations present in lungs 14 days post-inoculation with wild-type or RB50ΔbtrS. Standard high dose inoculation with wild-type RB50 only slightly increased B cell numbers in lungs compared with the non-infected control, whereas RB50ΔbtrS increased B cells numbers in lungs two-fold (FIGS. 7A-7C). The anti-*B. bronchiseptica* serum antibody titers induced by the mutant were measurably higher as early as day 7 post-infection. This is a striking finding, since antibodies to *Bordetellae* are generally not detected this early after infection and suggests that btrS mediates some B cell suppressive mechanisms that *Bordetellae* use to reduce antibody titers. Additionally, the mutant induced significantly higher anti-*B. bronchiseptica* IgA and IgG antibody titers in the lung homogenate 14 days post-infection, indicating that these effects accumulate over the course of infection (FIGS. 7A-7C).

Figure 8:
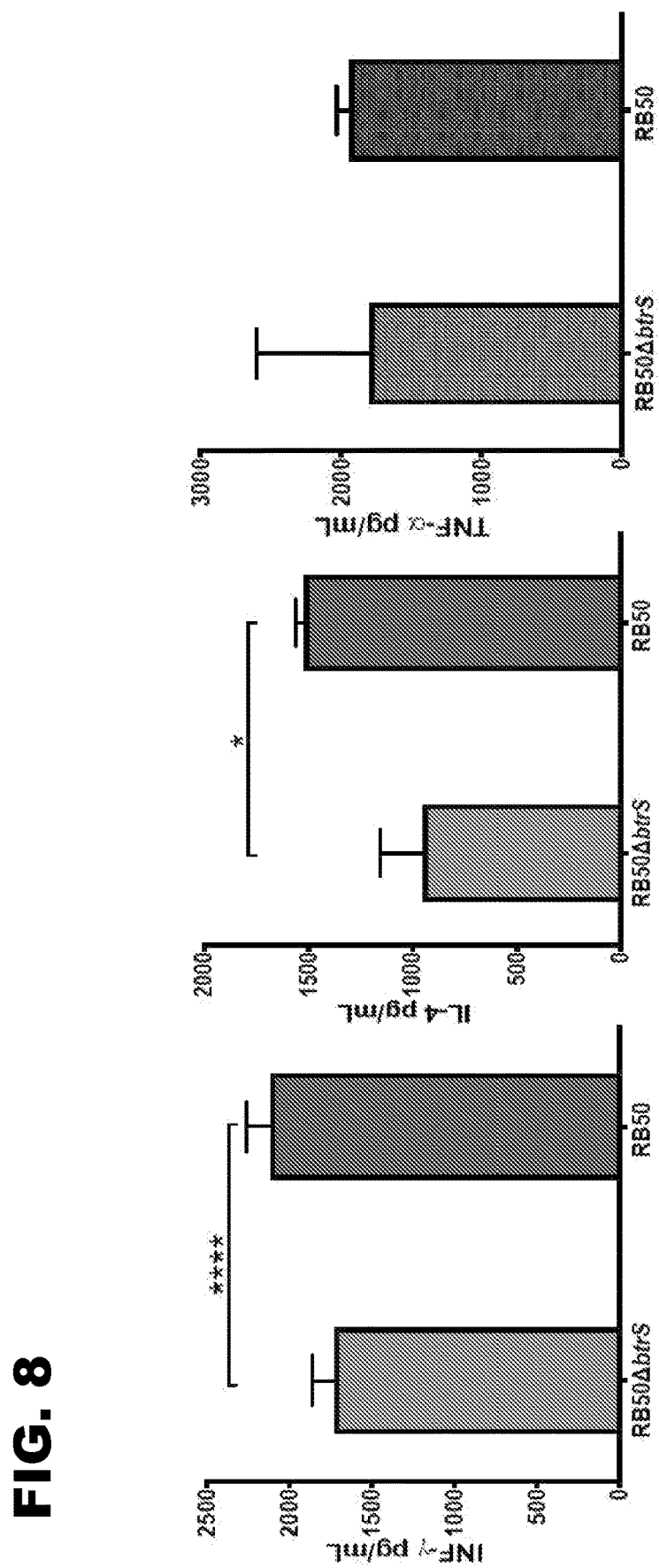
FIG. 8. The btrS mutant induces sterilizing immunity against *Bordetella bronchiseptica*. Shown in pg/ml are the cytokines produced by RAW 264.7 challenged with RB50ΔbtrS and RB50. The MOI was 1:100 and the macrophages were exposed to bacteria during 4 hours. Statistical significance was calculated using Two-Way Anova *=p<0.1 and ****=p<0.0001.

BtrS blocks effective sterilizing immunity to classical *Bordetellae*. The results above support the hypothesis that BtrS is induced by exposure to signals in blood/serum and turns on the expression of immunomodulatory functions that dampen the adaptive immune response, allowing longer persistence. Reasoning that these effects could be mediated by interactions with phagocytic antigen presenting cells, we investigated the effects of BtrS on macrophage signaling by exposing RAW 264.7 macrophages to wild type or mutant bacteria (MOI 1:100) and measuring IL-4 (Th2 response), INF (stimulation of lymphocytes) and TNF (MAPK signaling pathway) 4 hours later. These results demonstrated that BtrS suppresses the production of IL-4 and INFγ, potentially modulating both inflammatory and subsequent adaptive immune response by altering cytokine production of phagocytic cells (FIG. 8).

Figure 9A:
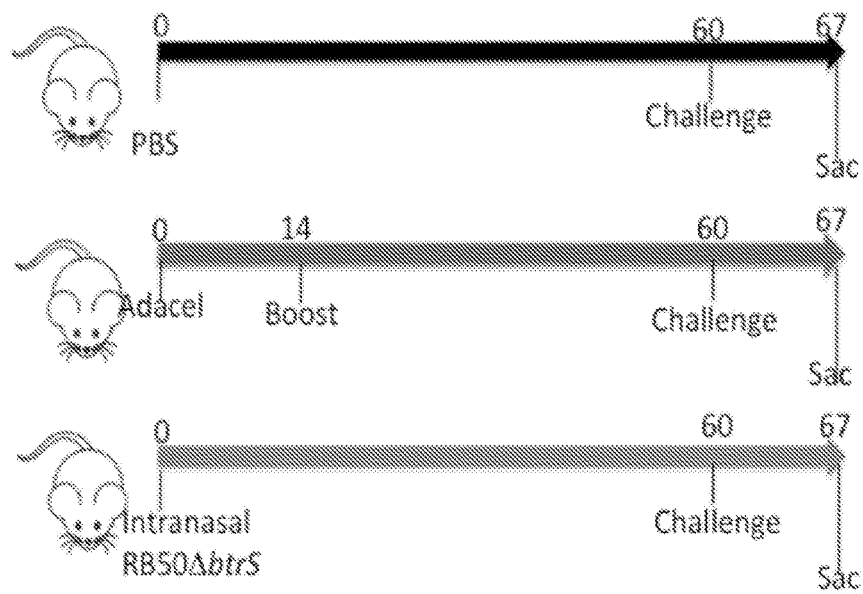
FIGS. 9A and 9B. The btrS mutant induces sterilizing immunity against *Bordetella bronchiseptica*.
Figure 9B:
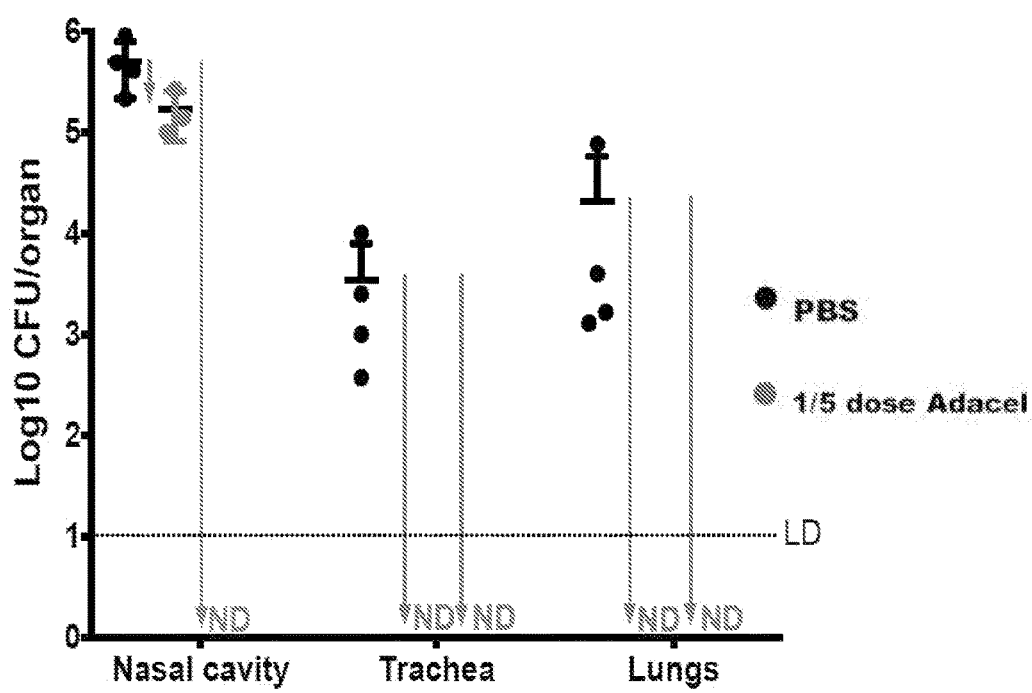

The RB50ΔbtrS mutant induces sterilizing protective immunity to *B. bronchiseptica*. To determine whether RB50ΔbtrS induces robust immunity that can protect against subsequent infection, groups of mice were either challenged with RB50ΔbtrS or vaccinated with the commercial acellular pertussis vaccine Adacel or PBS as a control. Two months later mice were intranasally challenged with $5 \times 10^5$ wild-type *B. bronchiseptica* in 50 µl of PBS (FIGS. 9A and 9B). PBS-treated mice (control group) showed high levels of colonization across the entire respiratory tract seven days post-inoculation. Mice previously vaccinated with the acellular vaccine had eliminated bacteria from the trachea and lungs, demonstrating the known protection against disease conferred by this vaccination. However, Adacel vaccination provided no significant reduction in the number of colonies isolated from the nasal cavity. Thus, despite conferring protection of the lower respiratory tract, the acellular vaccine does not stop colonization of the nasal cavity, allowing for transmission of the disease, as shown previously in mice (Smallridge et al., 2014, *J Infect Dis;* 209: 1981-1988) and baboons (Warfel et al., 2014, *Proc Natl Acad Sci USA;* 111: 787-792). Importantly, mice convalescent from challenge with the btrS mutant strain were completely free of *B. bronchiseptica* in lungs, trachea and nasal cavity, indicating that this mutant confers completely protective sterilizing immunity against *B. bronchiseptica* throughout the respiratory tract (FIGS. 9A and 9B). This is qualitatively and quantitatively greater protective immunity than has been previously reported for any vaccine against *B. bronchiseptica*.

Figure 10:
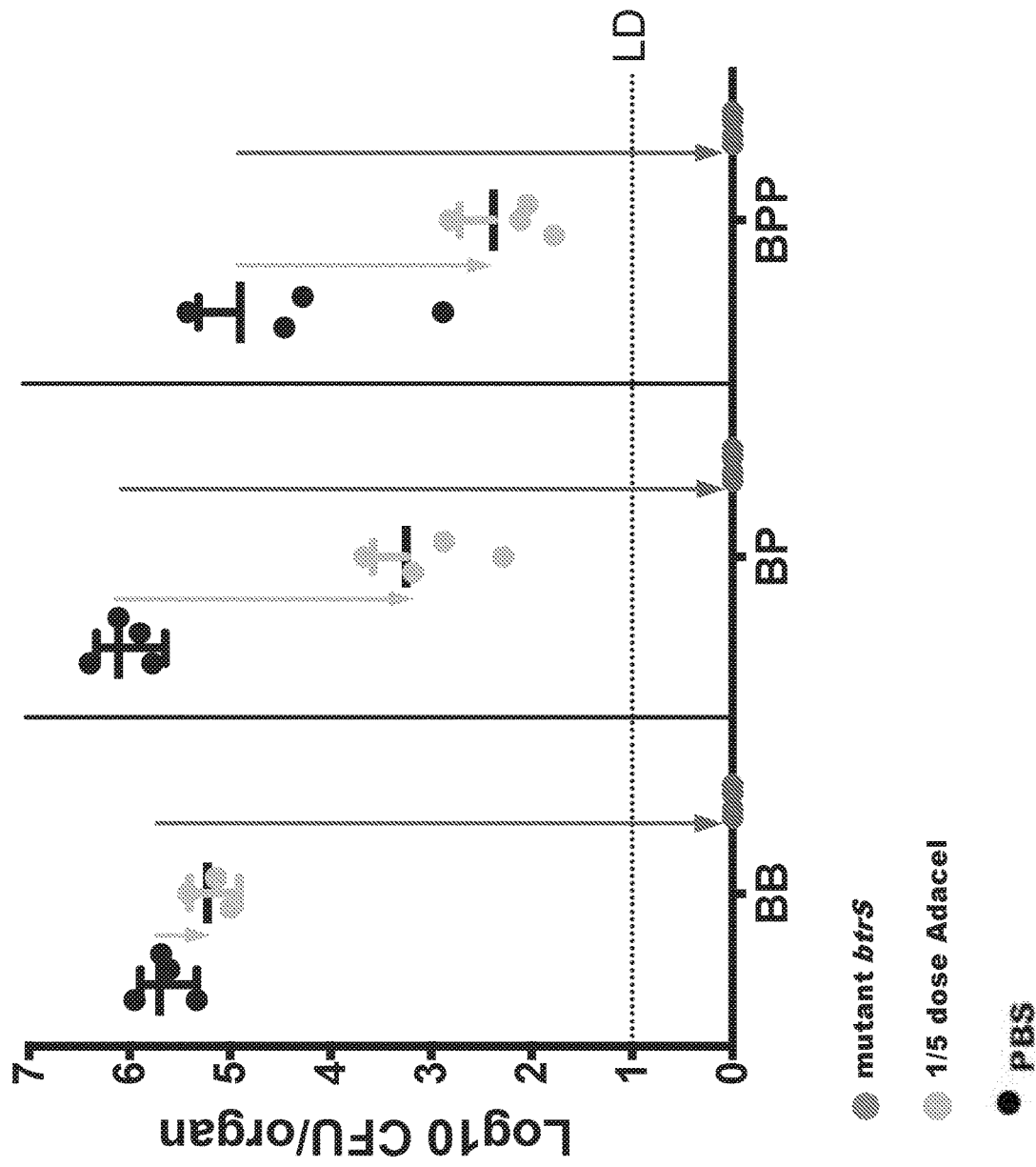
FIG. 10. RB50ΔbtrS induces sterilizing immunity against *B. pertussis* and *B. parapertussis*. Black circles indicate the PBS control group, grey circles indicate the group that was vaccinated with ⅕ of the dose of the current Adacel vaccine, and grey squares along the bottom axis indicate the group of the mice previously challenged with the mutant btrS. Statistical significance was calculated using Two-Way Anova ****=p<0.0001.

The RB50ΔbtrS mutant induces sterilizing protective immunity to *B. pertussis* and *B. parapertussis*. Since the immune response generated by the ΔbtrS mutant is substantially improved over that conferred by vaccines, we tested whether it could protect against the closely related and antigenically similar important human pathogens, *B. pertussis* and *B. parapertussis*. PBS treated mice challenged with *B. pertussis* or *B. parapertussis* contained high numbers of each in all respiratory organs (FIG. 10). Adacel vaccinate reduce the numbers of bacteria in the lower respiratory tract but all three *Bordetella* species persisted in the nasal cavity. These findings are consistent with clinical and laboratory findings that acellular vaccination confers protection against disease but is not completely successful at preventing colonization. In contrast, mice convalescent from prior exposure to the btrS mutant strain were completely protected against

*B. pertussis* and *B. parapertussis* disease and colonization, having developed fully sterilizing immunity against all three species (FIG. 10).

Figure 11A:
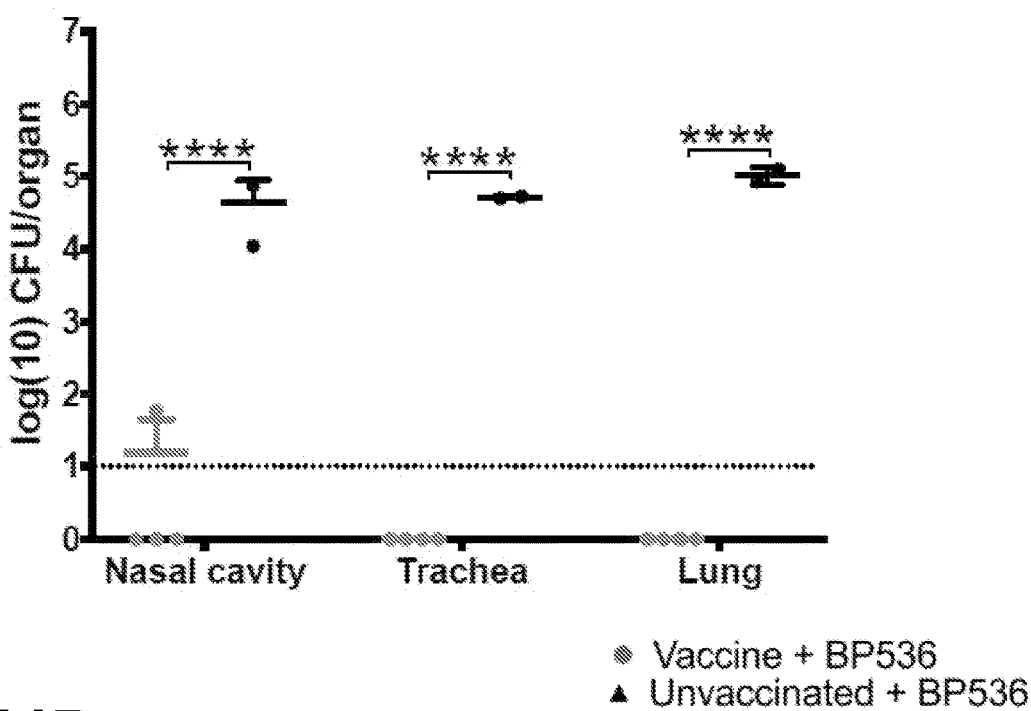
FIGS. 11A-11C. Low dose of RB50ΔbtrS can induce robust protection against classical *Bordetellae*.
Figure 11B:
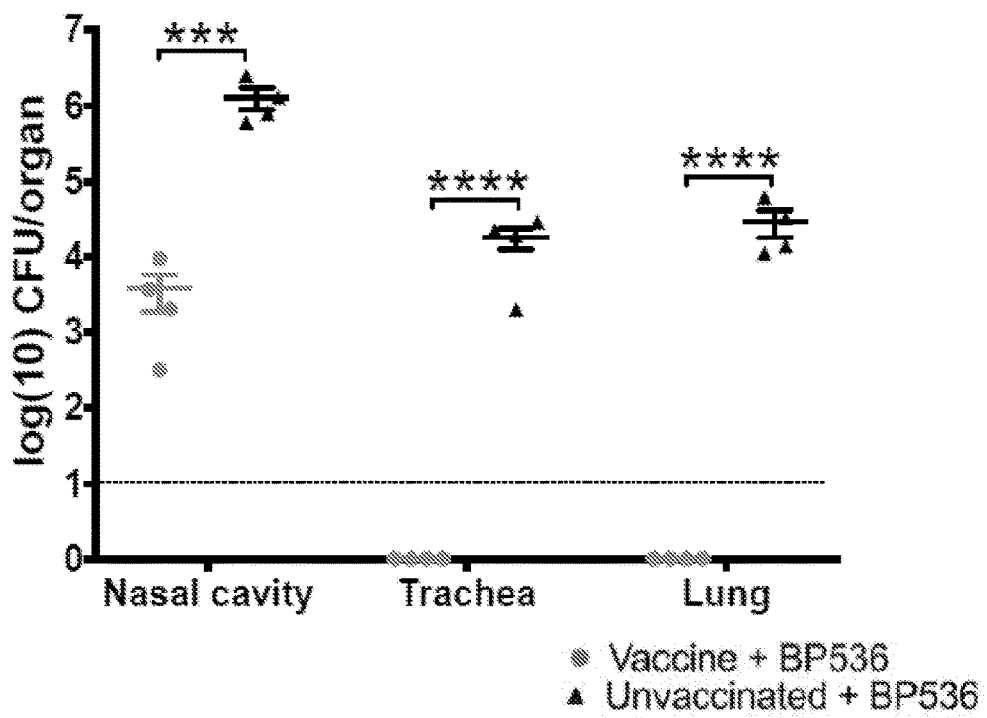
Figure 11C:
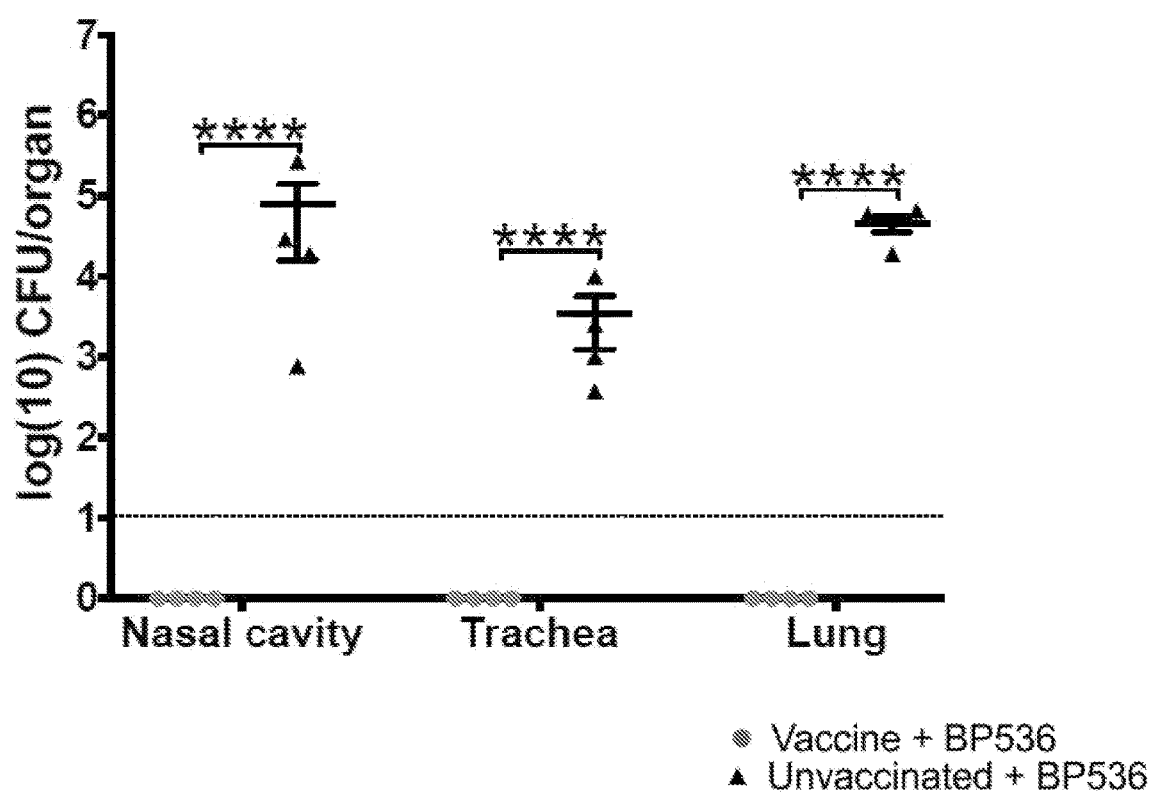

To determine if a low dose of RB50ΔbtrS will provide protection against the classical *Bordetella* strains, mice were challenged with 5 CFU of the mutant and were then intranasally challenged with high doses of either *B. bronchiseptica*, *B. pertussis*, or *B. parapertussis*. Even this very low dose of the RB50ΔbtrS mutant was sufficient to completely protect the trachea and lungs of all mice from all three species. Small numbers of *B. bronchiseptica* and *B. pertussis* were observed in the nasal cavities, indicating incomplete protection at this very low dose. But colonization was decreased relative to that seen in mice vaccinated with the commercial acellular pertussis vaccine, Adacel (FIGS. 11A-11C). This indicates that even a very small inocula of the RB50ΔbtrS is sufficient to elicit a robust and protective immune response and immunity against both *B. pertussis* and *B. parapertussis*.

To summarize, we discovered that previous challenge with RB50ΔbtrS led to protection against the three classical *Bordetellae* in the entire respiratory tract including the nasal cavity, conferring sterilizing immunity against further infection with any of the three classical *Bordetellae*. Extraordinarily, this is the first *Bordetella* spp. mutant that confers sterilizing immunity against not only *B. bronchiseptica* but also other *Bordetella* species.

Discussion

Despite under-reporting, recent increases in total cases and regional outbreaks of whooping cough have led both CDC and NIH to prioritize efforts at a response. Vaccines developed to protect against disease are effective in preventing illness in fully and recently vaccinated individuals but do not prevent colonization and transmission, allowing the pathogens to continue to spread. The observed increase in the mean age of infection (Kilgore et al., 2016, *Clin Microbiol Rev;* 29:449-486) is of concern, as is the risk to newborns before vaccination can protect them from disease. Thus, despite the widespread use with high coverage of vaccines that protect against disease, the failure to protect against infection allows the pathogen to continue to circulate. Without a strategy to provide complete, sterilizing immunity, it is hard to envision that an altered vaccine would have much impact. Adding another antigen is unlikely to change the basic problem that such vaccines protect against disease, but do not provide herd immunity by preventing colonization of individuals and circulation within populations. This example reports on a putative regulator that is induced by blood, serum and when *Bordetella* spp. are intracellular in macrophages, are implicated in regulation of immunomodulation.

Current vaccines were designed on the assumption that immune response generated by infection is the "gold standard" against which vaccines should be measured. However, well-adapted pathogens that persist or re-infect have tools to modulate the immune system and there is strong and consistent selection against presentation to the immune system of antigens that can confer protective immunity (Liu et al., 2012, *Mucosal Immunol;* 5:320-331; VanCott et al., 1998, *Nat Med;* 4:1247-1252; and Ercoli et al., 2018, *Nat Microbiol;* 3:600-610). From this standpoint, the view that the measure of the ideal vaccine should be how closely it resembles convalescent immunity is flawed. In this work we present evidence that there are substantial undiscovered *Bordetella* mechanisms for immunomodulation and that these appear to be carefully choreographed in response to exposure to blood and immune cells. Deleting a single regulator disrupts this profound modulation of adaptive immunity, leading to substantially better protective immunity.

This example demonstrates that a robust immune response that provides sterilizing immunity and cross-protection against different species of the same genus is achievable. These data support the view that *Bordetella* spp. vaccines can be substantially improved and opens the door to further analysis of the mechanisms of this more protective immunity. Understanding how *Bordetella* spp. prevent effective adaptive immunity will likely inform our views of the reasons for incomplete or imperfect sterilizing immunity against these and likely other pathogens.

Example 5

Livestock Vaccine Against *Bordetella* Species

*Bordetella* spp. infections constitute a great burden in agricultural livestock settings, but the current live attenuated vaccine lacks efficiency and only provides limited immunity. Outbreaks of *Bordetella* spp. infections have been reported in pigs, sheep, horses and poultry as well as other mammals. As shown in the previous examples, RB50Δbsr (also referred to herein as RB50ΔbrpL, RB50ΔbtrS and Bbvac), a new genetically engineered attenuated strain of *Bordetella bronchiseptica* confers sterilizing immunity against several *Bordetella* species including *B. bronchiseptica*, which is the major cause of athropic rhinitis and other respiratory diseases. The RB50Δbsr vaccine strain has been tested in mice and the results indicate RB50Δbsr confers robust protection.

With this example, pre-clinical trials will be performed to evaluate the protection conferred by this strain against the several *Bordetella* species that cause diseases in various animals. The nature of the immune protection conferred will then be determined. First, T cell populations and antibody response in C57 wild-type mice will be evaluated by monitoring the levels of IgA and IgG pre-vaccine, post-vaccine and post-challenge. Similarly, T cell populations and antibody response (IgA and IgG) will be evaluated using heat-killed bacteria as a vaccine. Finally, a cat model will be used to evaluate the RB50Δbsr vaccine using antibody titters as a marker to evaluate protection and response to the challenge. This example will provide us an improved, more efficient and robust vaccine against *Bordetella* spp. infection in livestock.

Background

Bordetellosis, atrophic rhinitis (de Jong, 1991, *Tijdschr Diergeneeskd;* 116(24):1221-30), and Kennel cough are caused by *Bordetella* spp., mainly *B. bronchiseptica* (McCandlish et al., 1976, *Vet Rec;* 98(8):156-7). These respiratory diseases affect a broad range of animals including, but not limited to, pigs (Duncan et al., 1966, *Am J Vet Res;* 27(117):457-66), horses (Mohan and Obwolo, 1991, *Trop Anim Health Prod;* 23(3):155-6; and Leissinger et al., 2013, *Vet Clin Pathol;* 42(4):529-30), sheep, poultry and aquatic life (Leissinger et al., 2013, *Vet Clin Pathol;* 42(4):529-30). In many cases, the disease begins as rhinitis or bronchitis, but due to co-infection or host factors, can progress to fatal bronchopneumonia. The disease can be transmitted to humans, and cases have been reported of cross-transmission between animals and their caretakers (Rath et al., 2008, *Clin Infect Dis;* 46(6):905-8). Bordetellosis can cause a high burden in domestic livestock, which are essential to the nation's food supply and the welfare of producers and consumers of animal products. Unfortunately, there is no good vaccine available. The vaccines that are presently on the market confer only limited protection and are not recommended for most animals. For example, there is no vaccine for equine or poultry. In addition, the available vaccines do not protect against all *Bordetella* strains, and the strength and length of protection after vaccination is suboptimal (Smith et al., 1982, *Res Vet Sci;* 32(2):248-52; Sakano et al., 1984, *Am J Vet Res;* 45(9):1814-7; and de Jong et al., 1987, *Vet Q;* 9(1):49-59).

As shown in the previous examples, RB50Δbsr, a genetically engineered strain of *B. bronchiseptica*, delivered intranasally in low dose, is a remarkably effective live vaccine, conferring sterilizing immunity against all three classical *Bordetella* species, *B. bronchiseptica, B. pertussis* and *B. parapertussis*. This example will study the strength and spectrum of protection. Pre-clinical studies will be performed in mice (a natural host of *B. bronchiseptica*) to assess the strength and coverage of protection and to evaluate cross-protection against other *Bordetella* spp. It is expected that RB50Δbsr will be a safe and effective vaccine that can readily be used in animal production settings. First, the immune response of vaccinated mice challenged with *B. bronchiseptica* will be characterized. Second, the immune response of vaccinated mice challenged with *B. avium* will be characterized.

Aim 1—Investigate the strength of protection of the RB50Δbsr vaccine strain against *Bordetella bronchiseptica* and other classical *Bordetellae*. To determine if RB50Δbsr confers stronger and longer-lasting protection than current vaccines, mice will be vaccinated with the RB50Δbsr vaccine strain, with the current vaccine (Nobivac Intra-Trac KC-Intranasal 25 ds Tray, Kennel-Jec 2 Nasal Vaccine for Dogs and Puppies w/Dropper, Solo-Jec KC Single Dose or Bronchicine CAe, 10 ds vial), or with a PBS control and then challenged with *B. bronchiseptica* 60 days post vaccination. T cell populations as well IgG and IgA antibody titers will be evaluated pre-vaccination, 3, 7, 10, 14 and 21 days post-vaccination and after challenge with *B. bronchiseptica* to study response patterns and to determine memory protection conferred by the vaccine. Thus, the efficacy of the RB50Δbsr engineered vaccine strain in comparison with the current vaccine and determine the efficiency of the response will be determined.

C57B6/L wild-type mice 4-6 weeks old will be vaccinated and challenged to evaluate the protection conferred by RB50Δbsr. Pre-samples will be taken to establish baseline antibody titers (IgA and IgG) against *B. bronchiseptica* in naive mice. Mice will be exposed to: 1)

RB50Δbsr vaccine (a genetically engineered strain RB50Δbsr), 2) the current vaccine (*Bordetella bronchiseptica* Intranasal (MVP); Rhini Shield TX4; Ingelvac AR4 or Parapleuro Shield P+BE), or 3) a PBS control group. Antibody titers (IgA and IgG) will be measured at days 7, 21, 35, 49 and 60 post-vaccination.

After 60 days post-vaccination, mice will be challenged with *B. bronchiseptica* to test protective immunity, by quantifying T cell populations (from lung and spleen using Flow cytometer), antibody titters (IgA and IgG) and CFU in respiratory tract organs at days 3, 7, 10, 14, and 21 post-challenge. This will test the efficiency of the RB50Δbsr our genetically engineered strain in comparison with the current vaccines and to characterize the immune response that confers better protection.

Aim 2. Investigate the strength of protection and coverage of the RB50Δbsr vaccine strain against *B. avium* and other non-classical *Bordetellae*. As shown in the previous examples, RB50Δbsr, a genetically engineered strain of *B. bronchiseptica* can fully protect, conferring sterilizing immunity against different *Bordetella* species (*B. bronchiseptica, B. pertussis* and *B. parapertussis*), making it the first vaccine that has a broad spectrum of protection as well as the only vaccine that confers sterilizing immunity. It is expected that RB50Δbsr will also confer strong protection against other non-classical *Bordetella* spp. To test this, mice will be vaccinated with the RB50Δbsr vaccine strain, with PBS (mock control) or the current vaccine. After 60 days, the mice will be challenged with *B. avium*. Different T cell populations and IgG and IgA titers will be evaluated prior to and after vaccination as well as after challenge with *Bordetella* strains to study response patterns and cross protection. Memory response will be evaluated after challenge with *B. avium*. This will test the efficiency of the RB50Δbsr engineered vaccine strain in comparison with the current vaccine and determine the efficiency of the response.

C57B6/L wild-type mice 4-6 weeks old will be used to evaluate the protection conferred by RB50Δbsr against *B. avium*. Pre-bleed samples will be collected to study antibody titers (IgA and IgG) against *B. avium* in naive mice. Mice will be first exposed to: 1) the RB50Δbsr vaccine (s genetically engineered strain), 2) the current vaccine (live attenuated *B. avium* non-resistant strain), and 3) a PBS control group. Antibody titers (IgA and IgG) will be measured at days 7, 21, 35, 49 and 60 post-vaccination.

After 60 days post-vaccination mice will be challenges with *B. avium* to test protective immunity, by quantifying T cell populations (from lung and spleen using Flow cytometer), antibody titters (IgA and IgG) and CFU in respiratory tract organs at days 3, 7, 10, 14, and 21 post-challenge. This will allow the testing of the efficiency of the RB50Δbsr genetically engineered strain in comparison with the current vaccines and determine the efficiency of the response.

Example 6

Novel and More Efficient Vaccine Against Feline Bordetellosis

*Bordetella bronchiseptica* infection of dogs, most commonly known as Kennel cough, is very common and several vaccines are available and required by most kennels. Although studies have shown that sero-prevalence of *B. bronchiseptica* in cats in the US is 47%, and Bordetellosis can progress to fatal bronchopneumonia, no vaccine is currently available for cats. As shown in the previous examples, RB50Δbsr (also referred to herein as RB50ΔbrpL, RB50ΔbtrS and Bbvac), is the genetically engineered a strain of *B. bronchiseptica* that confers robust, sterilizing immunity against *B. bronchiseptica*, making it a promising vaccine candidate. With this example, RB50Δbsr will be tested as a vaccine that can provide robust protection against *B. bronchiseptica* infection in felines. Pre-clinical trials will be performed to evaluate the protection conferred by RB50Δbsr in comparison to the commercially available dog vaccine. Antibody (both IgA and IgG) levels and T-cell responses will be characterized. Protective antigens will be identified to allow for further refinement of vaccines. Finally, RB50Δbsr will be tested in cats and the protection conferred by Bbvac compared to that from the standard dog vaccine.

Upper respiratory infections are the most serious type of ailment in cats. The bacterium *Bordetella bronchiseptica*, which is known as the causative agent of Kennel Cough in dogs, has been frequently isolated from cats with tracheobronchitis, rhinitis conjunctivitis and pneumonia and has been recognized as one of the main causative agents of respiratory problems in the feline population (Garbal et al., 2016, *Pol J Vet Sci;* 19(2):353-8; Foley et al., 2002, *Prev Vet Med;* 54(2):141-56; Bannasch and Foley, 2005, *J Feline Med Surg;* 7(2):109-19; and Helps et al., 2005, *Vet Rec;* 156(21):669-732-4). Bordetellosis is particularly dangerous in co-infection with other pathogens, including *Mycoplasma* species and herpesvirus, and can culminate in fatal bronchopneumonia. The most severe Bordetellosis affects young cats, encompassing 64% of all feline deaths (Welsh, 1996, *J Am Anim Hosp Assoc;* 32(2):153-8). There are few studies about the prevalence and epidemiology of this diseases within the feline population (Garbal et al., 2016, *Pol J Vet Sci;* 19(2):353-8). *B. bronchiseptica* has a prevalence as high as 46% among cats in California (Foley et al., 2002, *Prev Vet Med;* 54(2):141-56) indicating that nearly half of the cat population represents a reservoir for these bacteria and is at risk of developing disease, particularly within the first weeks of their life.

Interestingly, cats recovering from infection were shown to shed *B. bronchiseptica* intermittently without showing clinical symptoms (Coutts et al., 1996, *Vet Microbiol;* 48(1-2):19-27), indicating that they were still able to transmit the bacteria to other animals and thus spread the disease. Although dog vaccines were developed long ago (Bercovich and De Jong, 1977, *Tijdschr Diergeneeskd;* 102(7):448-55 and Phillips, 1980, *Vet Rec;* 106(4):89) and kennels generally require their use, the protection conferred by them is yet not clear (Ellis, 2015, Vet J; 204(1):5-16). Limited published data suggest that these widely used vaccines may help to control symptoms and to decrease tissue damage (Kobisch and Pennings, 1989, *Vet Rec;* 124(3):57-61; de Jong et al., 1987, *Vet Q;* 9(1):49-59; and de Jong 1987, *Vet Q;* 9(2): 123-33), but the protection period can be as short as 6 months. Recent vaccine studies have focused on improving delivery and penetration by using nanotechnology, mainly chitosan (Kang et al., 2008, *Microbiol Biotechnol;* 18(6): 1179-85 and Jiang et al., 2004, *Eur J Pharm Biopharm;* 58(3):471-6) but there is a lack of research focused on the development of novel vaccines.

The previous examples demonstrate that transient colonization with a genetically engineered strain of *B. bronchiseptica* (RB50Δbsr) induces sterilizing immunity against *B. bronchiseptica*. This example includes pre-clinical studies to better define immunological mechanisms in mice and then demonstrate effective protection from disease and from carriage in cats. Together, these aims will result in compelling evidence that RB50Δbsr can serve as an effective vaccine against feline bordetellosis that can prevent both disease and carriage.

This example will first characterize the immune response of vaccinated mice challenged with *B. bronchiseptica*. Secondly, it will demonstrate that the novel vaccine strain protects against infection with a broad variety of *B. bronchiseptica* representing the genetic variability of the species. And finally, it will include a pilot study using the RB50Δbsr vaccine in cats. The completion of this proposal will provide robust results to promote this novel vaccine to clinical trials.

Research Design and Methods

Aim 1. Determine the strength of protection of RB50Δbsr against *Bordetella bronchiseptica*. Based on data sown in the previous examples, the genetically engineered strain RB50Δbsr can protect against further colonization with *B. bronchiseptica* by conferring sterilizing immunity. It is expected that RB50Δbsr will provide strong immune protection and can be used as a vaccine to prevent Bordetellosis. To test this hypothesis, a mouse model will be used, noting that both cats and mice are natural hosts for *B. bronchiseptica*. *B. bronchiseptica*-specific T-cell populations as well as IgG and IgA antibody titers will be evaluated and protection against challenge with *B. bronchiseptica* assessed. This aim will evaluate the efficiency of the genetically engineered vaccine RB50Δbsr in comparison with the currently used dog vaccine in generating protective immunity.

4-6 weeks old C57B6/L wild-type mice will be vaccinated and challenged to evaluate the protection conferred by strain RB50Δbsr. Pre-vaccination blood samples will be collected to establish baseline antibody titers (IgA and IgG) against *B. bronchiseptica* in naive mice. Anesthetized mice will be 1) exposed to the potential vaccine strain Bbvac by pipetting 25 µl PBS containing 150 bacteria (CFU—Colony Forming Units) into the external nares, or 2) treated with PBS (mock control), or 3) vaccinated by application of the currently used vaccine Nobivac Intra-Trac KC onto the external nares. Nobivac Intra-Trac KC is a modified live intranasal vaccine containing attenuated canine parainfluenza virus and *Bordetella bronchiseptica* avirulent live culture for the vaccination of healthy susceptible puppies and dogs for prevention of canine infectious tracheobronchitis ("kennel cough") due to canine parainfluenza virus and *B. bronchiseptica*. Before Nobivac Intra-Trac KC is used, the bacterial numbers will be determined in the preparation by sequential plating and the concentration of the inoculum will subsequently be adjusted to contain 150 CFU in 25 µl.

At days 7, 21, 35, 49 and 60 post-vaccination blood will be collected (by cheek bleed) from all three groups of mice to measure antibody titers (IgA and IgG). 60 days post-vaccination, when strain RB50Δbsr has been cleared from all respiratory organs including the nasal cavity, anesthetized mice will be challenged with *B. bronchiseptica* strain RB50 by pipetting 150 CFU 25 µl onto the external nares. Groups of mice will be euthanized with $CO_2$ followed by cervical dislocation at days 3, 7, 10, 14, and 21 post-challenge to test the conferred immunity by quantifying B cell and T cell populations (from lung and spleen using Flow cytometer), antibody titers (IgA and IgG) and bacterial numbers in respiratory tract organs. This will allow for an estimate of the efficiency of the potential vaccine strain RB50Δbsr in comparison to the Nobivac Intra-Trac KC live vaccine and to characterize the immune response that confers protection against infection with *B. bronchiseptica*.

Aim 2. Test protective immunity against various *B. bronchiseptica* strains. Based on data presented in the previous examples, that RB50Δbsr can protect against further colonization with *B. bronchiseptica* by conferring sterilizing immunity, it is expected that RB50Δbsr will protect against colonization by any other *B. bronchiseptica* strains. To test this, protection against challenge with multiple different *B. bronchiseptica* strains that represent the genetic variation of the species will be assessed.

The protection provided by strain RB50Δbsr will be accessed by challenging vaccinated mice with different *B. bronchiseptica* strains. To this end, groups of 6 mice vaccinated with RB50Δbsr and 3 mice with PBS (mock control) will be challenged 60 days post vaccination with either of 12 *B. bronchiseptica* strains that represent the genetic variation of the species in terms of nucleotide diversity, gene content and host range. 7 days (3×Bbvac and 3×PBS) post-challenge and 14 day post challenge (3×RB50Δbsr), mice will be euthanized and *B. bronchiseptica* numbers in the nasal cavity and lungs will be enumerated to evaluate whether Bbvac protected against colonization.

Aim 3. Test protective immunity provided by strain RB50Δbsr in a cat model. Based on data presented in the previous examples, demonstrating robust sterilizing immunity in mice, it is expected that RB50Δbsr will provide a robust immune protection to prevent Bordetellosis in felines. This will be tested by vaccinating cats with either RB50Δbsr or the currently used dog vaccine and will evaluate T-cell response and antibody titers and protection from challenge with *B. bronchiseptica*. These data will provide for a comparison of RB50Δbsr and the currently used vaccine in their efficiency of providing protection.

The cat part of this proposal will be performed under close supervision of an animal resources veterinarian, adhering to the highest standards of animal work. To minimize animal discomfort, the cats will be lightly sedated for all procedures, including blood draws and inoculation with the vaccine and challenge strains.

Three cats will be vaccinated intranasally with the currently used dog vaccine Nobivac Intra-Trac KC using half the dosage recommended for dogs, and 3 cats will be vaccinated with a similar CFU the vaccine strain RB50Δbsr. Blood samples will be taken from the jugular vein pre-vaccine and at days 7, 21, 35, 49 and 60 post-vaccination to estimate antibody titers and T cell populations. The pre-vaccination samples are essential to confirm a negative serology and to establish a baseline in cats. While the cats are sedated, nasal swabs will be collected at the same days, using a Dacron-polyester swab (30 swipes), to enumerate the bacteria recovered from the external nares by dilution plating of resuspended swab samples on BG agar. The shedding of bacteria from mouse nares over time can be monitored using this approach and this measure of shedding strongly correlates with colonization (Rolin et al., 2014, *Infect Immun;* 82(2):491-9 and Rolin et al., 2014, *PLoS One;* 9(1):e85229). This same approach will be used in the case of this example. At day 60 post vaccination, the vaccinated animals will be challenged with *B. bronchiseptica* strain RB50 with a similar CFU than the previously administered vaccine.

At days 7, 14, 21 post challenge, nasal swabs and blood will be collected to assess bacterial colonization (from the nasal swabs) as well as T cells response and antibody titers (from blood). From these data it will be assessed whether the vaccines allowed colonization or prevented it by providing sterilizing immunity. In addition, it will provide for a comparison of RB50Δbsr and the currently used vaccine in their efficiency of providing protection against bordetellosis in felines.

At the end of the experiment, it is anticipated that cats vaccinated with RB50Δbsr will be *B. bronchiseptica*-free. In contrast, cats vaccinated with the commercially available dog vaccine will likely carry bacteria from the challenge. Infected cats will be cured from *B. bronchiseptica* colonization by treatment with antibiotics.

Example 7

Vaccine Against *B. pertussis* and Other Human Bordetellae

This example will develop a broader and more protective vaccine against *Bordetella pertussis, B. parapertussis,* and *B. homelsii*. The increase in the recent years of whooping cough despite the high vaccination rates forces the need of a novel and more effective vaccine that protects not only against symptoms but also colonization and transmission. This example will test vaccine safety, strength and length of protection of the RB50Δbsr (also referred to herein as RB50ΔbrpL, RB50ΔbtrS, and Bbvac) vaccine first in a robust mouse model. Then, parameters will be further assessed in the baboon model that is the accepted model to study pertussis vaccine prior clinical trials.

In this example a novel and more efficient vaccine against whooping cough and whooping cough like disease (*B. parapertussis* and *B. homelsii*) will be developed by using a live recombinant bacteria, which historically have been proven to be more efficient generating long-lasting immunity. Disrupting bacterial immune-modulators is expected to induce better and longer lasting immune response. Results of the previous examples show that the genetically engineered strain (RB50Δbsr) confers long lasting protection and sterilizing immunity against diverse *Bordetella* spp. including *B. bronchiseptica, B. pertussis*, and *B. parapertussis*. Importantly, no other vaccine in development has successfully protected against all classical *Bordetellae*. RB50Δbsr induces an earlier and more robust immune response increasing numbers of neutrophil, macrophages and CD4 and CD8 in lung; as well as increasing differentiation in spleen of those cells. These are all immune cells that have been previously identified as key in *B. pertussis* clearance. Interestingly the B cells number is also higher in lung and spleen and using western blot, novel bands that are recognized as novel antigens in BP can be recognized when using sera raised against RB50Δbsr. First, in this example, the dosage needed to induce sterilizing immunity, the length of protection, the immune response generated and the safety of the RB50Δbsr vaccine (by testing in mice lacking one or more components of the immunity) will be determined in a robust mouse model. Second, pilot studies will be started in baboons to test the strength and length of protection of RB50Δbsr, in comparison with the current acellular vaccine, the whole cell vaccine and a control group.

As shown in the previous examples, the genetically engineered strain RB50Δbsr confers long lasting protection and sterilizing immunity against diverse *Bordetella* spp. including *B. pertussis* and *B. parapertussis* (great human threats), indicating that it can be further developed as a vaccine. RB50Δbsr provides more effective and robust protection than the current acellular vaccine to prevent pertussis disease. This example will take a major step towards the development of a new vaccine that protects against *B. pertussis, B. parapertussis,* and *B. homelsii* in human populations. The main objectives are to perform studies using a robust mouse model to determine the strength and length of the protection and a first pilot study in a non-primate model, which will provide sufficient data to proceed to clinical trials with this novel vaccine candidate. This example includes the following objectives/aims.

Aim 1. Determine the strength and length of protection of RB50Δbsr. As shown in the previous example, RB50Δbsr confers sterilizing immunity against different species of *Bordetellae*. It is expected that RB50Δbsr will provide a robust immune protection against several clinical isolates of pertussis and provide a safe vaccine that confers robust protection. This example will first optimize the dose of RB50Δbsr needed to induce a sterilizing immune protection. Secondly, this example will study the protection against clinical strains of *B. pertussis, B. parapertussis,* and *B. homelsii*. Finally, this example will use immunocompromised mice to study the safety of RB50Δbsr.

Aim 2. Determine the strength and length of protection of RB50Δbsr in a baboon model. Based on the results of the previous examples, it is expected that RB50Δbsr is a better vaccine than the current acellular vaccine to confer long lasting and robust immune protection. To test this, baboons will be vaccinated with the current vaccine (an acellular vaccine), whole cell vaccine, RB50Δbsr, or with PBS (mock control). Three months later, baboons will be challenged with *B. pertussis* D240 and clinical isolates of *B. pertussis*. Different T cell populations and IgM, IgG, and IgA titers will be evaluated prior to and after vaccination as well as after challenge to study response patterns and cross protection.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A vaccine composition effective for inducing sterilizing immunity against *Bordetella bronchiseptica, Bordetella pertussis*, or *Bordetella parapertussis* in a vertebrate subject, the vaccine composition comprising an effective amount of an isolated strain of a *Bordetella* species and a pharmaceutically acceptable carrier suitable for administration to a vertebrate subject,
   wherein the isolated strain of the *Bordetella* species consists of a single mutation,
   wherein the single mutation prevents expression of the bsr sigma factor (also known as the btrS gene product or the brpL gene product),
   wherein the *Bordetella* species is selected from *Bordetella bronchiseptica, Bordetella pertussis*, or *Bordetella parapertussis*, and
   wherein sterilizing immunity prevents colonization in the lung and/or nasal cavity of the subject and prevents further transmission.

2. The vaccine composition of claim 1, wherein the vaccine composition is formulated for intranasal, oral, intradermal, or intramuscular administration to the vertebrate subject.

3. The vaccine composition of claim 1, wherein the sterilizing immunity comprises cross-protective immunity against a different *Bordetella* species selected from *Bordetella bronchiseptica, Bordetella pertussis*, or *Bordetella parapertussis*.

4. A vaccine composition effective for inducing sterilizing immunity against *Bordetella bronchiseptica, Bordetella pertussis*, or *Bordetella parapertussis* in a vertebrate subject, the vaccine composition comprising an effective amount of an isolated strain of a *Bordetella* species and a pharmaceutically acceptable carrier suitable for administration to a vertebrate subject,
   wherein the isolated strain of the *Bordetella* species comprises a mutation preventing expression of the bsr sigma factor (also known as the btrS gene product or the brpL gene product) and does not comprise a mutation in a gene of the adenylate cyclase toxin (CyaA) locus,
   wherein the *Bordetella* species is selected from *Bordetella bronchiseptica, Bordetella pertussis*, or *Bordetella parapertussis*, and
   wherein sterilizing immunity prevents colonization in the lung and/or nasal cavity of the subject and prevents further transmission.

5. The vaccine composition of claim 4, wherein the mutation comprises an in frame deletion of the gene encoding the bsr sigma factor.

6. The vaccine composition of claim 4, wherein the *Bordetella* species comprises *Bordetella bronchiseptica* strain RB50.

7. The vaccine composition of claim 4, wherein the vaccine composition is formulated for intranasal, oral, intradermal, or intramuscular administration to the vertebrate subject.

8. The vaccine composition of claim 4, wherein the sterilizing immunity comprises cross-protective immunity against a different *Bordetella* species selected from *Bordetella bronchiseptica, Bordetella pertussis*, or *Bordetella parapertussis*.

9. A method of vaccinating a subject against *Bordetella bronchiseptica, B. pertussis*, or *B. parapertussis*, the method comprising administering the vaccine composition of claim 4 to the subject.

10. The vaccine composition of claim 1, wherein the mutation comprises an in frame deletion of the gene encoding the bsr sigma factor.

11. The vaccine composition of claim 1, wherein the *Bordetella* species comprises *Bordetella bronchiseptica* strain RB50.

12. The vaccine composition of claim 1, wherein the *Bordetella* species comprises *Bordetella bronchiseptica* and the mutation comprises an in frame deletion of the gene encoding the bsr sigma factor.

13. The vaccine composition of claim 12, wherein the isolated *Bordetella* species comprises the *Bordetella bronchiseptica* RB50 strain.

14. A method of vaccinating a subject against *Bordetella bronchiseptica, B. pertussis*, or *B. parapertussis*, the method comprising administering the vaccine composition of claim 1 to the subject.

15. The method of claim 14, comprising intranasal, oral, intradermal, or intramuscular administration.

16. The method of claim 14, wherein the subject is livestock or domestic pet.

17. The method of claim 16, wherein the subject is a cow, pig, chicken, dog, cat, sheep, or horse.

18. The method of claim 14, wherein the subject is a human.

\* \* \* \* \*

UNITED STATES PATENT AND TRADEMARK OFFICE
CERTIFICATE OF CORRECTION

PATENT NO. : 11,229,690 B2  Page 1 of 1
APPLICATION NO. : 16/647740
DATED : January 25, 2022
INVENTOR(S) : Harvill et al.

It is certified that error appears in the above-identified patent and that said Letters Patent is hereby corrected as shown below:

In the Specification

Column 1, Line 14, CA054660-01 should be -CA054660-.

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*